United States Patent
O'Connor et al.

(10) Patent No.: US 12,397,160 B2
(45) Date of Patent: Aug. 26, 2025

(54) IMPLANTABLE ELECTRODES WITH REMOTE POWER DELIVERY FOR TREATING SLEEP APNEA, AND ASSOCIATED SYSTEMS AND METHODS

(71) Applicant: Invicta Medical, Inc., Santa Clara, CA (US)

(72) Inventors: Richard W. O'Connor, Atherton, CA (US); Walter Joseph Stevens, San Jose, CA (US); Timothy A. Fayram, Gilroy, CA (US)

(73) Assignee: Invicta Medical, Inc., Santa Clara, CA (US)

( * ) Notice: Subject to any disclaimer, the term of this patent is extended or adjusted under 35 U.S.C. 154(b) by 0 days.

(21) Appl. No.: 18/637,262

(22) Filed: Apr. 16, 2024

(65) Prior Publication Data
US 2024/0366942 A1 Nov. 7, 2024

Related U.S. Application Data

(62) Division of application No. 17/518,414, filed on Nov. 3, 2021, now Pat. No. 11,986,658.
(Continued)

(51) Int. Cl.
*A61N 1/36* (2006.01)
*A61N 1/05* (2006.01)
(Continued)

(52) U.S. Cl.
CPC .......... *A61N 1/3611* (2013.01); *A61N 1/0548* (2013.01); *A61N 1/0558* (2013.01);
(Continued)

(58) Field of Classification Search
CPC .............. A61N 1/0558; A61N 1/36062; A61N 1/0593; A61N 1/0551; A61N 1/057;
(Continued)

(56) References Cited

U.S. PATENT DOCUMENTS

| | | | |
|---|---|---|---|
| 4,365,636 A | 12/1982 | Barker | |
| 4,558,704 A | 12/1985 | Petrofsky | |

(Continued)

FOREIGN PATENT DOCUMENTS

| | | |
|---|---|---|
| CA | 2477540 | 5/2005 |
| CA | 3166004 | 8/2021 |

(Continued)

OTHER PUBLICATIONS

Atkinson, Martin, "Anatomy for Dental Students," OUP Oxford Fourth Edition, Mar. 14, 2013, p. 298.
(Continued)

*Primary Examiner* — Paula J Stice
(74) *Attorney, Agent, or Firm* — Perkins Coie LLP

(57) ABSTRACT

Implantable electrodes with power delivery wearable for treating sleep apnea, and associated systems and methods are disclosed herein. A representative system includes non-implantable signal generator worn by the patient and having an antenna that directs a mid-field RF power signal to an implanted electrode. The implanted electrode in turn directs a lower frequency signal to a neural target, for example, the patient's hypoglossal nerve. Representative signal generators can have the form of a mouthpiece, a collar or other wearable, and/or a skin-mounted patch.

17 Claims, 12 Drawing Sheets

Related U.S. Application Data

(60) Provisional application No. 63/109,809, filed on Nov. 4, 2020.

(51) Int. Cl.
    *A61N 1/372* (2006.01)
    *A61N 1/378* (2006.01)
    *H02J 50/20* (2016.01)

(52) U.S. Cl.
    CPC ..... *A61N 1/36139* (2013.01); *A61N 1/36153* (2013.01); *A61N 1/36157* (2013.01); *A61N 1/36171* (2013.01); *A61N 1/36175* (2013.01); *A61N 1/37205* (2013.01); *A61N 1/3787* (2013.01); *H02J 50/20* (2016.02)

(58) Field of Classification Search
    CPC ............ A61N 1/0573; A61N 2001/058; A61N 2001/059; A61N 1/37518
    See application file for complete search history.

(56) References Cited

U.S. PATENT DOCUMENTS

| | | | |
|---|---|---|---|
| 4,830,008 A | 5/1989 | Meer | |
| 4,947,844 A | 8/1990 | McDermott | |
| 5,146,918 A | 9/1992 | Kallok et al. | |
| 5,190,053 A | 3/1993 | Meer | |
| 5,193,539 A | 3/1993 | Schulman | |
| 5,193,540 A | 3/1993 | Schulman | |
| 5,212,476 A | 5/1993 | Maloney et al. | |
| 5,265,624 A | 11/1993 | Bowman | |
| 5,284,161 A | 2/1994 | Karell | |
| 5,540,732 A | 7/1996 | Testerman | |
| 5,546,952 A | 8/1996 | Erickson | |
| 5,697,076 A | 12/1997 | Troyk et al. | |
| 5,792,067 A | 8/1998 | Karell | |
| 6,132,384 A | 10/2000 | Christopherson et al. | |
| 6,212,435 B1 | 4/2001 | Lattner | |
| 6,240,316 B1 | 5/2001 | Richmond et al. | |
| 6,251,126 B1 | 6/2001 | Ottenhoff et al. | |
| 6,269,269 B1 | 7/2001 | Ottenhoff et al. | |
| 6,345,202 B2 | 2/2002 | Richmond et al. | |
| 6,361,494 B1 | 3/2002 | Lindenthaler | |
| 6,582,441 B1 | 6/2003 | He et al. | |
| 6,587,725 B1 | 7/2003 | Durand et al. | |
| 6,618,627 B2 | 9/2003 | Lattner et al. | |
| 6,636,767 B1 | 10/2003 | Knudson | |
| 7,189,204 B2 | 3/2007 | Ni et al. | |
| 7,252,640 B2 | 8/2007 | Ni et al. | |
| 7,367,935 B2 | 5/2008 | Mechlenburg et al. | |
| 7,369,896 B2 | 5/2008 | Gesotti | |
| 7,369,991 B2 | 5/2008 | Manabe et al. | |
| 7,371,220 B1 | 5/2008 | Koh et al. | |
| 7,574,357 B1 | 8/2009 | Jorgensen et al. | |
| 7,620,451 B2 | 11/2009 | Demarais et al. | |
| 7,634,315 B2 | 12/2009 | Mashiach et al. | |
| 7,660,632 B2 | 2/2010 | Kirby et al. | |
| 7,672,728 B2 | 3/2010 | Libbus et al. | |
| 7,680,538 B2 | 3/2010 | Durand et al. | |
| 7,684,858 B2 | 3/2010 | He et al. | |
| 7,711,438 B2 | 5/2010 | Lattner et al. | |
| 7,761,167 B2 | 7/2010 | Bennett et al. | |
| 7,822,480 B2 | 10/2010 | Park et al. | |
| 7,882,842 B2 | 2/2011 | Bhat et al. | |
| 7,890,193 B2 | 2/2011 | Tingey | |
| 7,920,915 B2 | 4/2011 | Mann | |
| 8,024,044 B2 | 9/2011 | Kirby et al. | |
| 8,200,486 B1 | 6/2012 | Jorgensen et al. | |
| 8,249,723 B2 | 8/2012 | McCreery | |
| 8,340,785 B2 | 12/2012 | Bonde et al. | |
| 8,359,108 B2 | 1/2013 | McCreery | |
| 8,498,712 B2 | 7/2013 | Bolea | |
| 8,574,164 B2 | 11/2013 | Mashiach | |
| 8,577,464 B2 | 11/2013 | Mashiach | |
| 8,577,478 B2 | 11/2013 | Mashiach et al. | |
| 8,585,617 B2 | 11/2013 | Mashiach et al. | |
| 8,620,438 B1 | 12/2013 | Wijting | |
| 8,655,451 B2 | 2/2014 | Klosterman | |
| 8,684,925 B2 | 4/2014 | Manicka et al. | |
| 8,688,219 B2 | 4/2014 | Ransom | |
| 8,768,474 B1 | 7/2014 | Thompson et al. | |
| 8,774,943 B2 | 7/2014 | McCreery et al. | |
| 8,812,130 B2 | 8/2014 | Stahmann et al. | |
| 8,855,767 B2 | 10/2014 | Faltys et al. | |
| 8,909,351 B2 | 12/2014 | Dinsmoor et al. | |
| 8,938,299 B2 | 1/2015 | Christopherson et al. | |
| 8,983,572 B2 | 3/2015 | Ni | |
| 8,983,611 B2 | 3/2015 | Mokelke et al. | |
| 9,031,653 B2 | 5/2015 | Mashiach | |
| 9,042,995 B2 | 5/2015 | Dinsmoor | |
| 9,061,162 B2 | 6/2015 | Mashiach et al. | |
| 9,136,728 B2 | 9/2015 | Dinsmoor | |
| 9,155,899 B2 | 10/2015 | Mashiach et al. | |
| 9,205,255 B2 | 12/2015 | Strother | |
| 9,227,053 B2 | 1/2016 | Bonde et al. | |
| 9,248,302 B2 | 2/2016 | Mashiach et al. | |
| 9,308,381 B2 | 4/2016 | Mashiach et al. | |
| 9,402,563 B2 | 8/2016 | Thakur et al. | |
| 9,409,013 B2 | 8/2016 | Mashiach | |
| 9,415,215 B2 | 8/2016 | Mashiach | |
| 9,415,223 B2 | 8/2016 | Carbunaru et al. | |
| 9,463,318 B2 | 10/2016 | Mashiach et al. | |
| 9,486,628 B2 | 11/2016 | Christopherson et al. | |
| 9,504,828 B2 | 11/2016 | Mashiach et al. | |
| 9,586,048 B2 | 3/2017 | Ternes et al. | |
| 9,643,022 B2 | 5/2017 | Mashiach et al. | |
| 9,687,664 B2 | 6/2017 | Poon et al. | |
| 9,808,620 B2 | 11/2017 | Kent | |
| 9,833,613 B2 | 12/2017 | Sama | |
| 9,839,786 B2 | 12/2017 | Rondoni et al. | |
| 9,849,289 B2 | 12/2017 | Mashiach et al. | |
| 9,855,431 B2 | 1/2018 | Ternes | |
| 9,888,864 B2 | 2/2018 | Rondoni et al. | |
| 9,889,299 B2 | 2/2018 | Ni et al. | |
| 9,895,541 B2 | 2/2018 | Meadows et al. | |
| 9,907,967 B2 | 3/2018 | Mashiach et al. | |
| 9,943,391 B2 | 4/2018 | Chu | |
| 9,950,166 B2 | 4/2018 | Mashiach et al. | |
| 10,004,913 B2 | 6/2018 | Poon et al. | |
| 10,052,097 B2 | 8/2018 | Mashiach et al. | |
| 10,058,701 B2 | 8/2018 | Sama | |
| 10,195,426 B2 | 2/2019 | Kent | |
| 10,195,427 B2 | 2/2019 | Kent | |
| 10,195,428 B2 | 2/2019 | Scheiner | |
| 10,238,872 B2 | 3/2019 | Pivonka et al. | |
| 10,314,501 B2 | 6/2019 | Zitnik et al. | |
| 10,335,596 B2 | 7/2019 | Yakovlev et al. | |
| 10,512,782 B2 | 12/2019 | Mashiach et al. | |
| 10,583,297 B2 | 3/2020 | Ni | |
| 10,594,166 B2 | 3/2020 | Ho et al. | |
| 10,716,940 B2 | 7/2020 | Mashiach et al. | |
| 10,744,339 B2 | 8/2020 | Makansi | |
| 10,751,537 B2 | 8/2020 | Mashiach et al. | |
| 10,806,926 B2 | 10/2020 | Christopherson et al. | |
| 10,827,786 B2 | 11/2020 | Amour et al. | |
| 10,828,502 B2 | 11/2020 | Poon et al. | |
| 10,898,709 B2 | 1/2021 | Wagner et al. | |
| 10,932,682 B2 | 3/2021 | Christopherson et al. | |
| 10,967,183 B2 | 4/2021 | Yakovlev et al. | |
| 10,994,139 B2 | 5/2021 | Fayram et al. | |
| 11,033,738 B2 | 6/2021 | Steier | |
| 11,090,491 B2 | 8/2021 | Mashiach et al. | |
| 11,160,980 B2 | 11/2021 | Mashiach et al. | |
| 11,253,712 B2 | 2/2022 | Mashiach | |
| 11,266,837 B2 | 3/2022 | Scheiner et al. | |
| 11,273,305 B2 | 3/2022 | Scheiner et al. | |
| 11,291,842 B2 | 4/2022 | Caparso et al. | |
| 11,298,549 B2 | 4/2022 | Mashiach et al. | |
| 11,324,950 B2 | 5/2022 | Dieken et al. | |
| 11,964,154 B1 | 4/2024 | Raux | |
| 11,986,658 B2 | 5/2024 | O'Connor et al. | |
| 2001/0023362 A1 | 9/2001 | Kobayashi | |
| 2003/0069626 A1 | 4/2003 | Lattner et al. | |

(56) References Cited

U.S. PATENT DOCUMENTS

| | | |
|---|---|---|
| 2003/0195571 A1 | 10/2003 | Burnes et al. |
| 2003/0199945 A1 | 10/2003 | Ciulla |
| 2004/0073272 A1 | 4/2004 | Knudson |
| 2004/0147975 A1 | 7/2004 | Popovic |
| 2005/0038485 A1 | 2/2005 | Ludwig |
| 2005/0043644 A1 | 2/2005 | Stahmann et al. |
| 2005/0085874 A1 | 4/2005 | Davis |
| 2005/0137646 A1 | 6/2005 | Wallace |
| 2005/0261600 A1 | 11/2005 | Aylsworth |
| 2006/0155206 A1 | 7/2006 | Lynn |
| 2006/0247729 A1 | 11/2006 | Tehrani |
| 2006/0266369 A1 | 11/2006 | Atkinson et al. |
| 2007/0173893 A1 | 7/2007 | Pitts |
| 2007/0270632 A1 | 11/2007 | Nelson |
| 2007/0277836 A1 | 12/2007 | Longley |
| 2008/0033304 A1 | 2/2008 | Dalal |
| 2008/0103545 A1 | 5/2008 | Bolea |
| 2008/0103769 A1 | 5/2008 | Schultz et al. |
| 2008/0208287 A1 | 8/2008 | Palermo |
| 2009/0030469 A1* | 1/2009 | Meiry .................... A61N 1/372 607/9 |
| 2009/0118610 A1 | 5/2009 | Karmarkar et al. |
| 2009/0221943 A1 | 9/2009 | Burbank |
| 2010/0023103 A1 | 1/2010 | Elborno |
| 2010/0094376 A1 | 4/2010 | Penner |
| 2010/0094379 A1 | 4/2010 | Meadows |
| 2010/0094398 A1 | 4/2010 | Malewicz |
| 2010/0100153 A1 | 4/2010 | Carlson et al. |
| 2010/0152546 A1 | 6/2010 | Behan et al. |
| 2010/0152808 A1 | 6/2010 | Boggs, II |
| 2010/0185254 A1 | 7/2010 | Lindquist et al. |
| 2010/0201500 A1 | 8/2010 | Stirling et al. |
| 2010/0241195 A1 | 9/2010 | Meadows |
| 2010/0280570 A1 | 11/2010 | Sturm |
| 2011/0093032 A1 | 4/2011 | Boggs, II |
| 2011/0093036 A1 | 4/2011 | Mashiach |
| 2011/0112601 A1 | 5/2011 | Meadows et al. |
| 2011/0132378 A1 | 6/2011 | Levendowski |
| 2011/0152965 A1 | 6/2011 | Mashiach |
| 2011/0172733 A1 | 7/2011 | Lima et al. |
| 2011/0172743 A1 | 7/2011 | Davis et al. |
| 2011/0213438 A1 | 9/2011 | Lima et al. |
| 2011/0230702 A1 | 9/2011 | Honour |
| 2011/0264164 A1 | 10/2011 | Christopherson |
| 2011/0295083 A1 | 12/2011 | Doelling et al. |
| 2012/0024297 A1 | 2/2012 | Hedge |
| 2012/0029362 A1 | 2/2012 | Patangay et al. |
| 2012/0089153 A1 | 4/2012 | Christopherson |
| 2012/0192874 A1 | 8/2012 | Bolea |
| 2012/0197340 A1 | 8/2012 | Tesfayesus |
| 2012/0234331 A1 | 9/2012 | Totada |
| 2013/0072999 A1 | 3/2013 | Mashiach |
| 2013/0085537 A1 | 4/2013 | Mashiach |
| 2013/0085544 A1 | 4/2013 | Mashiach |
| 2013/0085545 A1 | 4/2013 | Mashiach |
| 2013/0085558 A1 | 4/2013 | Mashiach |
| 2013/0085559 A1 | 4/2013 | Mashiach |
| 2013/0085560 A1 | 4/2013 | Mashiach |
| 2013/0140289 A1 | 6/2013 | Barateir |
| 2013/0261693 A1 | 10/2013 | Gross |
| 2014/0046221 A1 | 2/2014 | Mashiach |
| 2014/0135868 A1 | 5/2014 | Bashyam |
| 2014/0228905 A1 | 8/2014 | Bolea |
| 2014/0236031 A1 | 8/2014 | Banet et al. |
| 2015/0029030 A1 | 1/2015 | Aoyama |
| 2015/0038865 A1 | 2/2015 | Shigeto |
| 2015/0039046 A1 | 2/2015 | Gross |
| 2015/0057719 A1 | 2/2015 | Tang |
| 2015/0073232 A1 | 3/2015 | Ahmed |
| 2015/0112697 A1 | 4/2015 | Bradley |
| 2015/0134028 A1 | 5/2015 | Greatbatch |
| 2015/0142120 A1 | 5/2015 | Papay |
| 2015/0182753 A1 | 7/2015 | Harris |
| 2015/0190630 A1 | 7/2015 | Kent et al. |
| 2015/0206151 A1 | 7/2015 | Carney |
| 2015/0224307 A1* | 8/2015 | Bolea ................ A61N 1/36057 607/42 |
| 2015/0273177 A1 | 10/2015 | Lizuka |
| 2015/0374991 A1 | 12/2015 | Morris et al. |
| 2016/0089540 A1 | 3/2016 | Bolea |
| 2016/0114159 A1 | 4/2016 | Kent |
| 2016/0235981 A1 | 8/2016 | Southwell |
| 2016/0317160 A1 | 11/2016 | Smith et al. |
| 2016/0317345 A1 | 11/2016 | Marie |
| 2016/0331952 A1 | 11/2016 | Faltys |
| 2017/0014068 A1 | 1/2017 | Gotoh et al. |
| 2017/0087360 A1 | 3/2017 | Scheiner |
| 2017/0095667 A1 | 4/2017 | Yakovelev et al. |
| 2017/0135604 A1 | 5/2017 | Kent |
| 2017/0135629 A1 | 5/2017 | Kent |
| 2017/0143257 A1 | 5/2017 | Kent |
| 2017/0143259 A1 | 5/2017 | Kent |
| 2017/0143280 A1 | 5/2017 | Kent |
| 2017/0143960 A1 | 5/2017 | Kent |
| 2017/0151432 A1 | 6/2017 | Christopherson |
| 2017/0224987 A1 | 8/2017 | Kent |
| 2017/0368341 A1 | 12/2017 | Bolea |
| 2018/0015282 A1* | 1/2018 | Waner ...................... A61B 5/00 |
| 2018/0085593 A1 | 3/2018 | Fayram et al. |
| 2018/0214079 A1 | 8/2018 | Banet et al. |
| 2018/0220921 A1 | 8/2018 | Rondoni et al. |
| 2018/0221660 A1 | 8/2018 | Suri et al. |
| 2019/0001139 A1 | 1/2019 | Mishra et al. |
| 2019/0022383 A1 | 1/2019 | Hadlock |
| 2019/0057700 A1 | 2/2019 | Kent |
| 2019/0060642 A1 | 2/2019 | Boggs, II et al. |
| 2019/0099285 A1 | 4/2019 | Bachelder et al. |
| 2019/0117967 A1 | 4/2019 | Scheiner |
| 2019/0374776 A1 | 12/2019 | Mishra et al. |
| 2020/0001077 A1 | 1/2020 | Kent |
| 2020/0016401 A1 | 1/2020 | Papay et al. |
| 2020/0038033 A1 | 2/2020 | Clark et al. |
| 2020/0054867 A1 | 2/2020 | Schwartz et al. |
| 2020/0054889 A1 | 2/2020 | Makansi |
| 2020/0069947 A1 | 3/2020 | Kent |
| 2020/0139138 A1 | 5/2020 | Sit |
| 2020/0281763 A1 | 9/2020 | Scheiner |
| 2020/0316373 A1 | 10/2020 | Bolea |
| 2020/0338358 A1 | 10/2020 | Makansi |
| 2020/0346010 A1 | 11/2020 | Papay et al. |
| 2020/0346016 A1 | 11/2020 | Caparso et al. |
| 2020/0346024 A1 | 11/2020 | Caparso et al. |
| 2020/0376261 A1 | 12/2020 | Stevens et al. |
| 2021/0052888 A1 | 2/2021 | Kent |
| 2021/0106824 A1 | 4/2021 | Caparso et al. |
| 2021/0321939 A1 | 10/2021 | Kent |
| 2022/0032052 A1 | 2/2022 | Kent et al. |
| 2022/0126103 A1 | 4/2022 | Pivonka et al. |
| 2022/0134101 A1 | 5/2022 | Scheiner et al. |
| 2022/0134102 A1 | 5/2022 | Kent |
| 2022/0161031 A1 | 5/2022 | Kent |
| 2022/0218988 A1 | 7/2022 | Caparso et al. |
| 2022/0339441 A1 | 10/2022 | Elliott |
| 2022/0346666 A1 | 11/2022 | Elliott |
| 2022/0362553 A1 | 11/2022 | Gouveris et al. |
| 2022/0370797 A1 | 11/2022 | O'Connor |
| 2022/0379114 A1 | 12/2022 | Kent |
| 2022/0401728 A1 | 12/2022 | Dassos et al. |
| 2022/0409897 A1 | 12/2022 | O'Connor |
| 2023/0026728 A1 | 1/2023 | Elliott |
| 2023/0172479 A1 | 6/2023 | Verzal |
| 2023/0240715 A1 | 8/2023 | Paspa et al. |
| 2023/0302280 A1 | 9/2023 | O'Connor |
| 2023/0321440 A1 | 10/2023 | O'Connor |
| 2023/0414945 A1 | 12/2023 | Ward |
| 2024/0307697 A1 | 9/2024 | Mullins et al. |

FOREIGN PATENT DOCUMENTS

| | | |
|---|---|---|
| CN | 201361029 | 12/2009 |
| EP | 1128868 | 3/2010 |
| JP | 2014158607 | 9/2014 |
| KR | 20060087852 | 8/2006 |
| KR | 10-2019-0049502 | 5/2019 |

(56) References Cited

FOREIGN PATENT DOCUMENTS

| WO | WO-9720522 | 6/1997 |
|---|---|---|
| WO | WO-2008100779 | 8/2008 |
| WO | WO-2010006218 | 1/2010 |
| WO | WO-2012027648 | 3/2012 |
| WO | WO-2013172935 | 11/2013 |
| WO | WO-2017070372 | 4/2017 |
| WO | 2017178694 | 10/2017 |
| WO | WO-2019140404 | 7/2019 |
| WO | WO-2020181120 | 9/2020 |
| WO | WO-2021050829 | 3/2021 |
| WO | WO-2021163228 | 8/2021 |
| WO | WO-2021216724 | 10/2021 |
| WO | WO-2021242633 | 12/2021 |
| WO | WO-2022058024 | 3/2022 |
| WO | 2022098786 | 5/2022 |
| WO | WO-2022129234 | 6/2022 |
| WO | WO-2022129236 | 6/2022 |
| WO | WO-2022129247 | 6/2022 |
| WO | 2023247333 | 12/2023 |

OTHER PUBLICATIONS

Benbassat et al., "The specific branches leading to the genioglossus muscle: three dimensional localisation using skin reference points," Surgical and Radiologic Anatomy, 2019, 9 pages.

Caycedo et al., "Electromyographic Analysis for Silent Speech Detection," ARPN Journal of Engineering and Applied Sciences, vol. 12, No. 1 Jan. 2017, 8 pages.

Delaey et al., "Specific branches of hypoglossal nerve to genioglossus muscle as a potential target of selective neurostimulation in obstructive sleep apnea: anatomical and morphometric study," Surg Radiol Anata, 2017, 9 pages.

Extended European Search Report for European Patent Application No. 21890006.6, Applicant: Invicta Medical, Inc., mailed Apr. 26, 2024, 8 pages.

Gharb et al., "Microsurgical Anatomy of the Terminal Hypoglossal Nerve Relevant for Neurostimulation in Obstructive Sleep Apnea," Neuromodulation: Technology at the Neural Interface, 2015, 8 pages.

Heiser et al., "Surgical anatomy of the hypoglossal nerve: A new classification system for selective upper airway stimulation," Wiley Periodicals, Inc., wileyonlinelibrary.com/journal/hed, 2017, 10 pages.

International Search Report and Written Opinion for International Patent Application No. PCT/US21/57936, Applicant: Invicta Medical, Inc., mailed Mar. 24, 2022, 21 pages.

Janke et al., "A Spectral Mapping Method for EMG-based Recognition of Silent Speech," In B-Interface, 2010, 10 pages.

Kent et al., "Ultrasound Localization and Percutaneous Electrical Stimulation of the Hypoglossal Nerve and Ansa Cervivalis," Otolaryngology Head and Neck Surgery, 2020, 7 pages.

Li et al., "Dynamic Drug-Induced Sleep Computed Tomography in Adults with Obstructive Sleep Apnea," Scientific Reports—www.nature.com/scientificreports, Oct. 2016, 8 pages.

Mu et al., "Human Tongue Neuroanatomy: Nerve Supply and Motor Endplates," National Institute of Health, 2012, 27 pages.

Pearse et al., "Review: Sleep-Disordered Breathing in Heart Failure," Imperial College London and Royal Brompton Hospital, London, United Kingdom, https://onlinelibrary.wiley.com/doi/full/10.1002/ejhf.492, published Feb. 11, 2016, 26 pages.

Vroegop et al., "Sleep endoscopy with simulation bite for prediction of oral appliance treatment outcome," Obstructive Sleep Apnea, European Sleep Research Society, 2012, 8 pages.

Weaker, Frank, "Structures of the Head and Neck," F.A. Davis, Sep. 24, 2013, p. 77.

Website: CawBing: Snore Stopper Adjustable Snore Reduction Straps Anti Apnea Snore Support Belt Jaw Sleep Band Snoring Chin Strap, https://www.walmart.com/ip/Snore-Stopper-Adjustable-Snore-Reduction-Straps-Anti-Apnea-Snore-Support-Belt-Jaw-Sleep-Band-Snoring-Chin-Strap/788742945, accessed Jun. 2022, 5 pages.

Website: Halo Chinstrap by Breathwear Inc., https://www.cpap.com/productpage/breathewear-halo-chinstrap, accessed Jun. 2022, 3 pages.

Wirth et al., "Hypogloassal nerve stimulation therapy does not alter tongue protrusion strength and fatigability in obstructive sleep apnea," Journal of Clinical Sleep Medicine, vol. 16, No. 2., Feb. 2020, 8 pages.

\* cited by examiner

IMPLANTABLE ELECTRODES WITH REMOTE POWER DELIVERY FOR TREATING SLEEP APNEA, AND ASSOCIATED SYSTEMS AND METHODS

CROSS REFERENCE TO RELATED APPLICATION

The present application is a divisional of U.S. patent application Ser. No. 17/518,414 filed Nov. 3, 2021, which claims priority to U.S. Provisional App. No. 63/109,809, filed Nov. 4, 2020 and incorporated herein by reference. To the extent the foregoing application and/or any other materials conflict with the present disclosure, the present disclosure controls.

TECHNICAL FIELD

The present technology is directed generally to implantable electrodes wirelessly coupled to a remote power delivery device for treating sleep apnea, and associated systems and methods. Representative power delivery devices include a mouthpiece, a device worn in a collar or other neck clothing forms, and/or an adhesive skin-mounted device.

BACKGROUND

Obstructive sleep apnea (OSA) is a medical condition in which a patient's upper airway is occluded (partially or fully) during sleep, causing sleep arousal. Repeated occlusions of the upper airway may cause sleep fragmentation, which in turn may result in sleep deprivation, daytime tiredness, and/or malaise. More serious instances of OSA may increase the patient's risk for stroke, cardiac arrhythmias, high blood pressure, and/or other disorders.

OSA may be characterized by the tendency for soft tissues of the upper airway to collapse during sleep, thereby occluding the upper airway. OSA is typically caused by the collapse of the patient's soft palate, oropharynx, tongue, epiglottis, or combination thereof, into the upper airway, which in turn may obstruct normal breathing and/or cause arousal from sleep.

Some treatments have been available for OSA including, for example, surgery, constant positive airway pressure (CPAP) machines, and electrically stimulating muscles or related nerves associated with the upper airway to move the tongue (or other upper airway tissue). Surgical techniques have included tracheotomies, procedures to remove portions of a patient's tongue and/or soft palate, and other procedures that seek to prevent the tongue from collapsing into the back of the pharynx. These surgical techniques are very invasive. CPAP machines seek to maintain upper airway patency by applying positive air pressure at the patient's nose and mouth. However, these machines are uncomfortable, cumbersome, and may have low compliance rates.

Some electrical stimulation techniques seek to prevent the tongue from collapsing into the back of the pharynx by causing the tongue to protrude forward (e.g., in an anterior direction) and/or flatten during sleep. However, existing techniques for electrically stimulating the nerves of the patient's oral cavity suffer from being too invasive, and/or not sufficiently efficacious. Thus, there is a need for an improved minimally-invasive treatment for OSA and other sleep disorders.

BRIEF DESCRIPTION OF THE DRAWINGS

Representative embodiments of the present technology are illustrated by way of example and are not intended to be limited by the Figures, in which like reference numerals generally refer to corresponding parts throughout.

DETAILED DESCRIPTION

Figure 1:
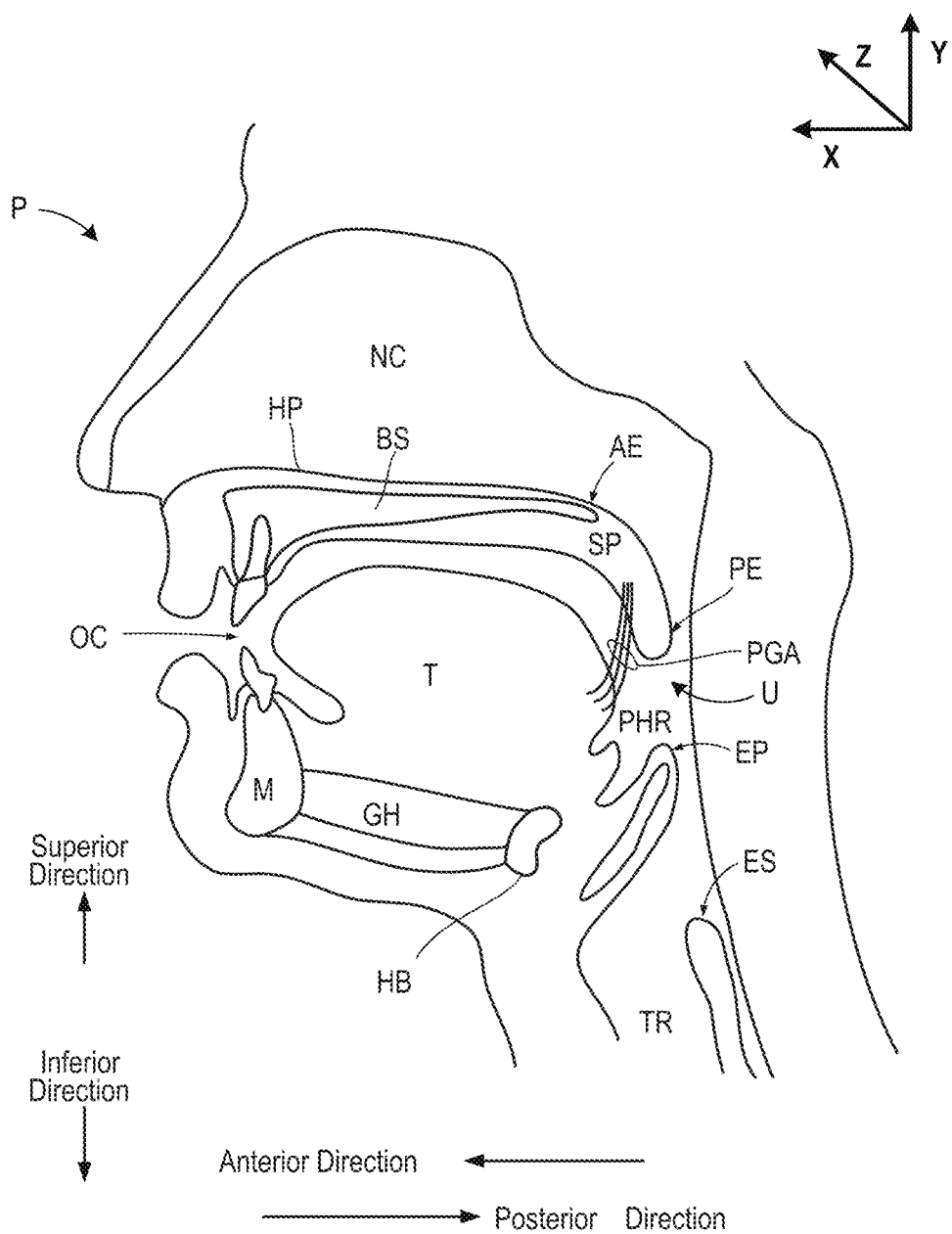
FIG. 1 is a side sectional view depicting a patient's upper airway.

The present technology is discussed under the following headings for ease of readability:

Heading 1: "Introduction"
Heading 2: "Representative Stimulation Targets" (with a focus on FIGS. 1-2B)
Heading 3: "Representative Devices and Methods" (with a focus on FIGS. 3A-7)
Heading 4: "Representative Waveforms" (with a focus on FIGS. 8A and 8B)

While embodiments of the present technology are described under the selected headings indicated above, other embodiments of the technology can include elements discussed under multiple headings. Accordingly, the fact that an embodiment may be discussed under a particular heading does not necessarily limit that embodiment to only the elements discussed under that heading.

1. Introduction

Electrical stimulation for obstructive sleep apnea (OSA) typically includes delivering an electrical current that modulates nerves and/or muscles, e.g., to cause the tongue and/or other soft tissue to move. The electrical stimulation can accordingly remove an obstruction of the upper airway, or prevent the tongue or other soft tissue from collapsing or obstructing the airway. As used herein, the terms "modulate" and "stimulate" are used interchangeably to mean having an effect on, e.g., an effect on a nerve that in turn has an effect on one or more motor functions, e.g., a breathing-related motor function.

Representative methods and apparatuses for reducing the occurrence and/or severity of a breathing disorder, such as OSA, are disclosed herein. In accordance with representative embodiments, a minimally-invasive signal delivery device is implanted proximate to or adjacent to nerves that innervate the patient's oral cavity, soft palate, oropharynx, and/or epiglottis. Representative nerves include the hypoglossal nerve, branches of the ansa cervicalis and/or the vagus nerves, which are located adjacent and/or around the oral cavity or in the neck. The signal delivery device can be implanted in the patient via a percutaneous injection. A non-implanted power source, e.g., including one or more mouthpiece portions, collar portions, chinstrap portions, pillow portions, mattress overlay portions, other suitable "wearables," and/or one or more adhesive, skin-mounted devices, can wirelessly provide electrical power to the implanted signal delivery device. The signal delivery device emits accurately targeted electrical signals (e.g., pulses) that improve the patient's upper airway patency and/or improve the tone of the tissue of the intraoral cavity to treat sleep apnea. The electrical current delivered by the signal delivery device can stimulate efferent, peripheral nerves, e.g., at least a portion of a patient's hypoglossal nerve and/or other nerves associated with the upper airway. By moving the tongue forward and/or by preventing the tongue and/or soft tissue from collapsing onto the back of the patient's pharynx, and/or into the upper airway, the devices and associated methods disclosed herein can in turn improve the patient's sleep, e.g., by moving the potentially obstructing tissue in the upper airway/pharynx down. More specifically, applying the electrical signal to the medial branch of the hypoglossal nerve can cause the tongue to move forward (anteriorly), and applying the electrical signal to the ansa cervicalis can cause the thyroid, larynx, trachea, and/or any of the tissues (e.g., cartilage) thereof, to move downward (inferiorly or caudally), a motion typically referred to as caudal traction. The system can also include one or more feedback and/or diagnostic devices or features that control the presence, timing, and/or manner in which the electrical therapy is provided to the patient. Accordingly, one or more sensors can detect patient characteristics (e.g., sleep state, wake state, and/or respiratory characteristics), which then can be used to meter the therapy, in real-time, or near real-time. As a result, the system can deliver the therapy to the neural target only when the patient is asleep, and/or only when the patient's respiratory performance (e.g., oxygen perfusion level) indicates that the therapy is necessary or helpful.

Many embodiments of the technology described below may take the form of computer- or machine- or controller-executable instructions, including routines executed by a programmable computer or controller. Those skilled in the relevant art will appreciate that the technology can be practiced on computer/controller systems other than those shown and described below. The technology can be embodied in a special-purpose computer, controller or data processor that is specifically programmed, configured or constructed to perform one or more of the computer-executable instructions described below. Accordingly, the terms "computer" and "controller" as generally used herein refer to any suitable data processor and can include Internet appliances and hand-held devices (including palm-top computers, wearable computers, tablets, cellular or mobile phones, multi-processor systems, processor-based or programmable consumer electronics, network computers, mini computers and the like). Information handled by these computers can be presented at any suitable display medium, including a liquid crystal display (LCD).

The present technology can also be practiced in distributed environments, where tasks or modules are performed by remote processing devices that are linked through a communications network. In a distributed computing environment, program modules or subroutines may be located in local and remote memory storage devices. Aspects of the technology described below may be stored or distributed on any suitable computer-readable media, including one or more ASICs, (e.g., with addressable memory), as well as distributed electronically over networks. Data structures and transmissions of data particular to aspects of the technology are also encompassed within the scope of the embodiments of the technology.

2. Representative Stimulation Targets

Representative embodiments described herein include signal delivery devices having electrodes that can be positioned to deliver one or more electrical currents to one or more specific target locations, e.g., specific nerves and/or specific positions along a nerve. FIG. 1 illustrates the general anatomy of the patient's oral cavity, and later Figures illustrate specific target locations. Such locations include locations along the patient's hypoglossal nerve, branches of the ansa cervicalis, and/or vagus nerves, as those nerves innervate muscles of airway (e.g., palatal, oropharyngeal, laryngeal muscles) besides the tongue. The target location can be identified with respect to any of, or any combination of, intrinsic or extrinsic muscles, associated nerve branches, and/or other physiological features. Such a target location and/or position can also be distal from the salivary glands (e.g., medial to the sublingual salivary gland) and/or other structures to avoid causing pain and/or other undesired effects.

FIG. 1 illustrates a patient P relative to a coordinate system in which the x-axis denotes the anterior-posterior directions, the y-axis denotes the superior-inferior directions, and the z-axis denotes the medial-lateral directions. The patient P has a hard palate HP which overlies the tongue T and forms the roof of the oral cavity OC (e.g., the mouth). The hard palate HP includes bone support BS, and thus does not typically deform during breathing. The soft palate SP, which is made of soft tissue such as membranes, fibrous material, fatty tissue, and muscle tissue, extends rearward (e.g., in a posterior direction) from the hard palate HP toward the back of the pharynx PHR. More specifically, an anterior end AE of the soft palate SP is anchored to a posterior end of the hard palate HP, and a posterior end PE of the soft palate SP is unattached. Because the soft palate SP does not contain bone or hard cartilage, the soft palate SP is flexible and may collapse onto the back of the pharynx PHR and/or flap back and forth (e.g., especially during sleep).

The pharynx PHR, which passes air from the oral cavity OC and the nasal cavity NC into the trachea TR, is the part of the throat situated inferior to (below) the nasal cavity NC, posterior to (behind) the oral cavity OC, and superior to (above) the esophagus ES. The pharynx PHR is separated from the oral cavity OC by the palatoglossal arch PGA, which runs downward on either side to the base of the tongue T. Although not shown for simplicity, the pharynx PHR includes the nasopharynx, the oropharynx, and the laryngopharynx. The nasopharynx lies between an upper surface of the soft palate SP and the wall of the throat (i.e., superior to the oral cavity OC). The oropharynx lies behind the oral cavity OC, and extends from the uvula U to the level of the hyoid bone HB. The oropharynx opens anteriorly into the oral cavity OC. The lateral wall of the oropharynx includes the palatine tonsil, and lies between the palatoglossal arch PGA and the palatopharyngeal arch. The anterior wall of the oropharynx includes the base of the tongue T and the epiglottic vallecula. The superior wall of the oropharynx includes the inferior surface of the soft palate SP and the uvula U. Because both food and air pass through the pharynx PHR, a flap of connective tissue called the epiglottis EP closes over the glottis (not shown for simplicity) when food is swallowed to prevent aspiration. The laryngopharynx is the part of the throat that connects to the esophagus ES, and lies inferior to the epiglottis EP. Below the tongue T is the lower jaw or mandible M, and the geniohyoid muscle GH, which is one of the muscles that controls the movement of the tongue T.

Figure 2A:
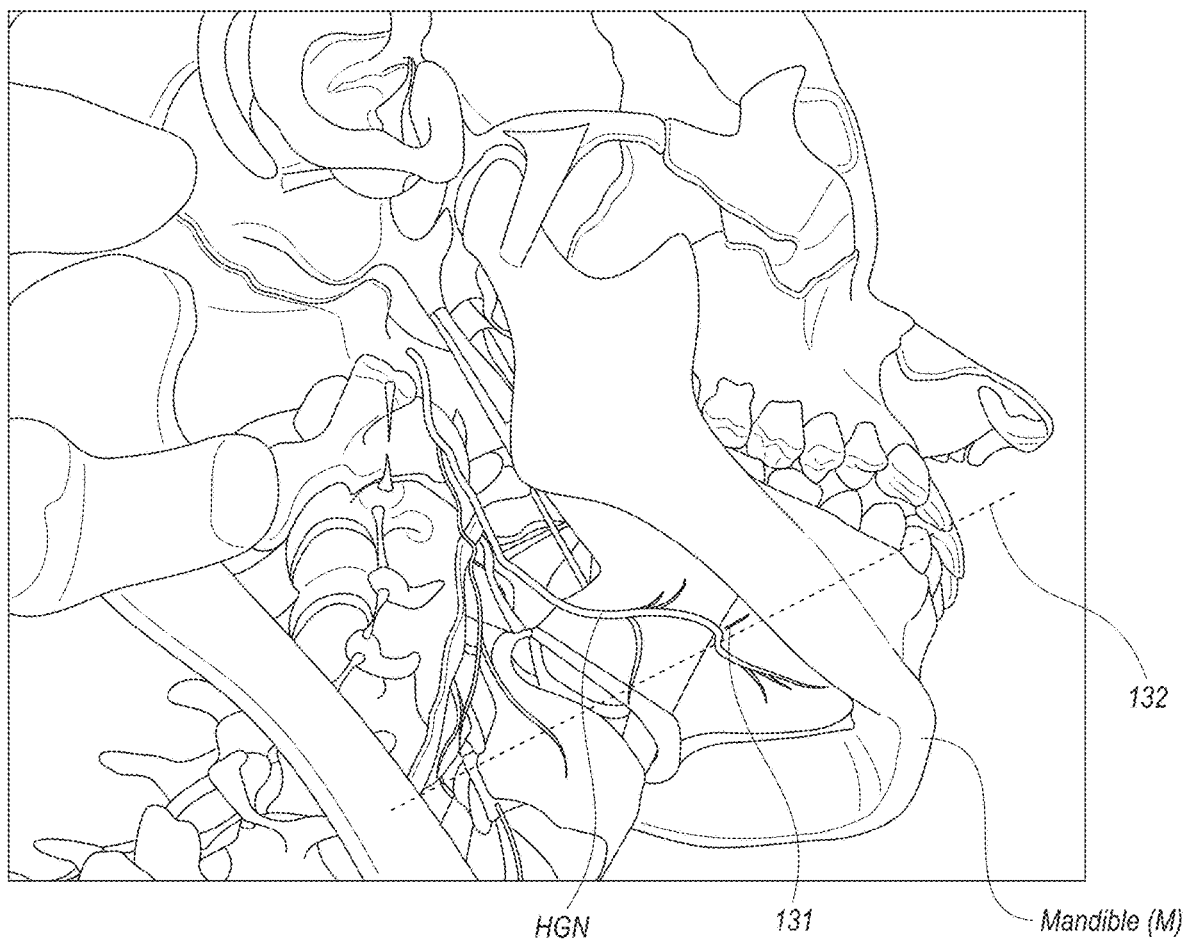
FIG. 2A is a view of a patient's skull, from below, illustrating the hypoglossal nerve and a representative electrode location in accordance with embodiments of the present technology.
Figure 2B:
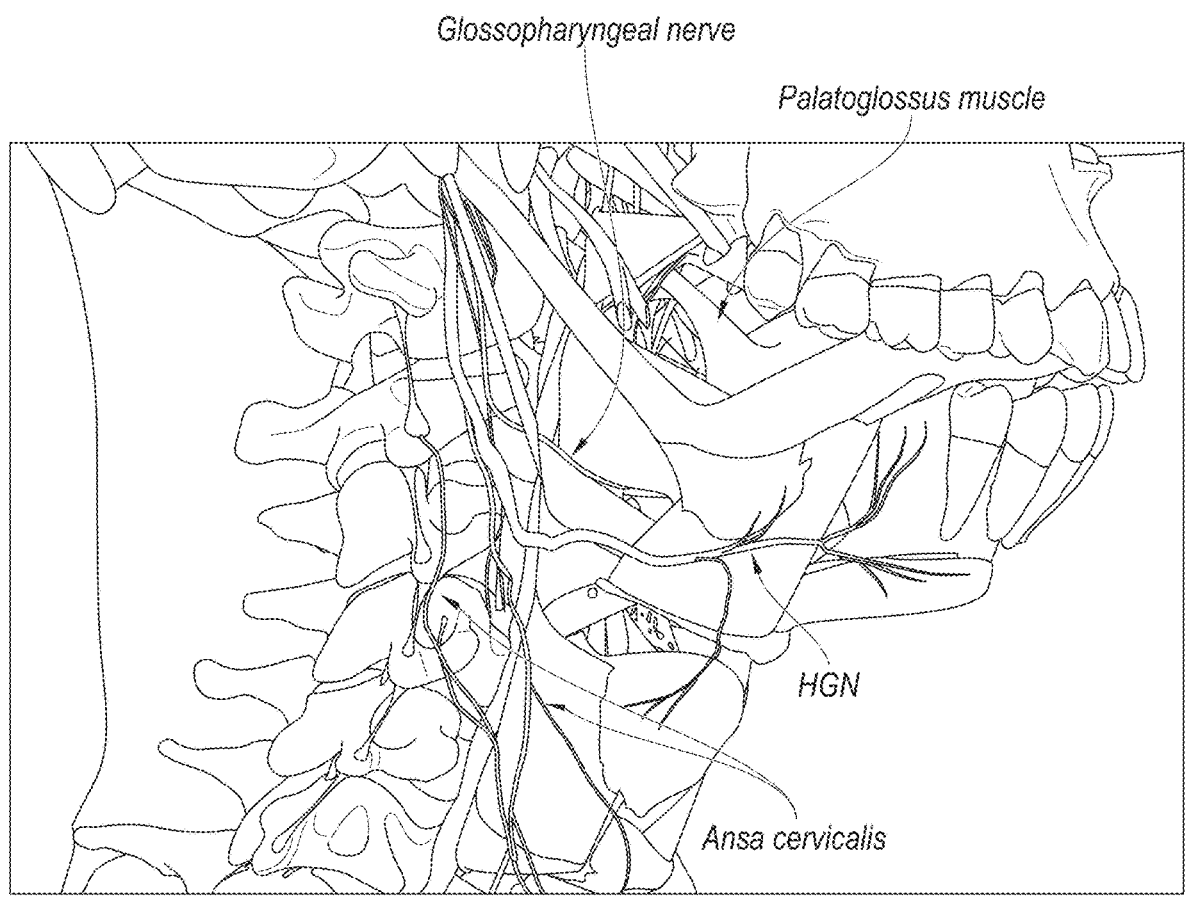
FIG. 2B is a side view of a patient's skull, illustrating further representative signal delivery targets in accordance with embodiments of the present technology.

FIG. 2A is a partially schematic, isometric illustration of the patient's skull, looking upwardly toward the mandible M. FIG. 2A also illustrates the hypoglossal nerve HGN which innervates the muscles controlling the patient's tongue T (FIG. 1). In representative embodiments, one or more electrodes 131 are positioned along the hypoglossal nerve HGN, in particular, at the medial branch of the HGN, in an electrode plane 132 defined by the medial branch. By precisely positioning the electrode(s) 131 within this plane 132, and adjacent to the hypoglossal nerve HGN, it is expected that systems in accordance with embodiments of the present technology can more effectively control the patient's airway patency, without causing discomfort, and/or other undesirable effects, and/or in a manner that reduces the amount of power required to produce effective therapy signals. As discussed elsewhere herein, other representative target nerves include the ansa cervicalis and vagal nerves. Still further representative targets include cranial nerves (e.g., the glossopharangeal nerve), and the palatoglossus muscle. FIG. 2B illustrates these targets. Representative systems for producing the foregoing and/or other outcomes via signals directed to the above targets are described further below with reference to FIGS. 3-8B.

3. Representative Devices and Methods

Figure 3A:
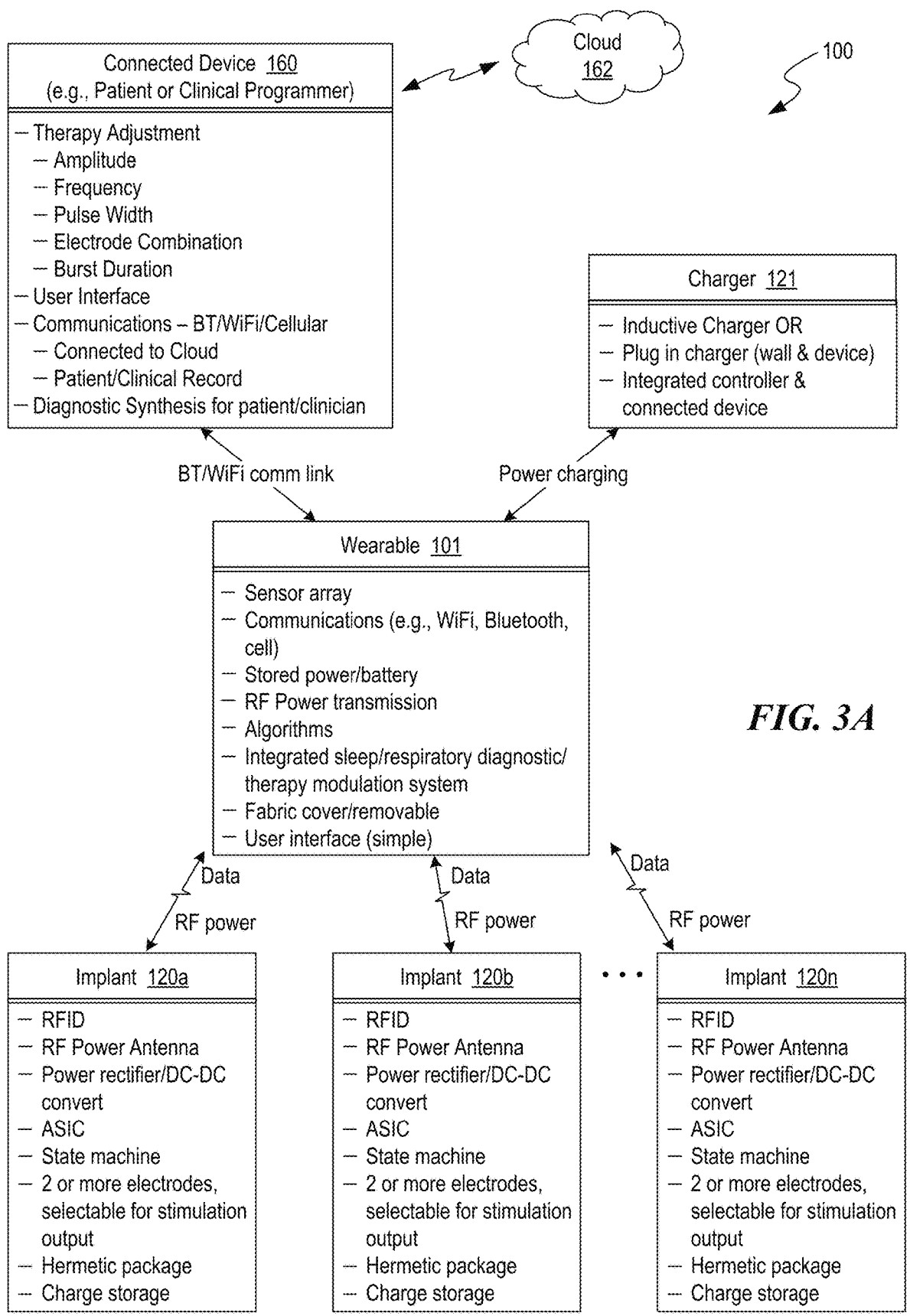
FIG. 3A is a block diagram illustrating elements of a system for treating sleeping disorders in accordance with embodiments of the present technology.

FIG. 3A is a block diagram illustrating elements of a system 100 for treating sleep disorders in accordance with embodiments of the present technology. The system 100 can include a wearable device 101, a charger 121, one or more implants or implantable devices (e.g., a first implantable device 120a, a second implantable device 120b . . . an n$^{th}$ implantable device 120n; referred to collectively as "implantable devices 120") and a connected device or programmer 160. In general, the programmer 160 can transmit instructions for generating an electrical signal (e.g., signal delivery or waveform parameters) to the wearable device 101, the wearable device 101 can transmit the instructions and power to the implantable device(s) 120, and individual ones of the implantable devices 120 can generate the electrical signal according to the transmitted instructions and apply the electrical signal to a patient via electrodes carried by the implantable device(s) 120. Many of the above-listed aspects of the system 100 are also described in greater detail below with reference to FIG. 3B.

The programmer 160 can include a patient-operated programmer and/or a clinician-operated programmer, and can be configured to control one or more characteristics of the electrical signal delivered to the patient. In a representative embodiment, the programmer 160 can include a therapy adjustment module configured to select individual ones of the electrodes carried by the implantable device(s) 120 and adjust (e.g., increase or decrease) an amplitude, frequency, pulse width, a burst duration, whether the electrode is active or inactive, and/or any other suitable signal delivery parameter. Additionally, the programmer 160 can synthesize information (e.g., diagnostic and/or feedback information) received from the wearable 101 and/or individual ones of the implantable devices 120, and can adjust one or more of the signal delivery parameters based at least partially on the synthesized information. The programmer 160 can transmit the signal delivery parameters to the implantable device(s) 120 directly and/or via the wearable device 101. For example, the programmer 160 can be connected to individual ones of the implantable devices 120 and/or the wearable device 101 via a wired or wireless communication link, such as WiFi, Bluetooth ("BT"), cellular connectivity, and/or any other suitable communication link. In these and other embodiments, the programmer 160 can be connected to a cloud 162 and/or other computer service, e.g., to upload data received from the wearable device's 101 sensors and/or to download information to the wearable device 101 and/or the implantable device(s) 120. In these and other embodiments, the programmer 160 can include a display and/or a user interface. A user (e.g., the patient, the clinician, and/or other suitable user) can interact with and/or otherwise control one or more aspects of the programmer 160 via the user interface, e.g., to manually adjust one or more of the signal delivery parameters, to read data received from the wearable device 101 sensors, and/or carry out other tasks.

The wearable device 101 can include one or more sensors (e.g., a single sensor, an array of sensors, and/or other suitable sensor arrangements) configured to collect data associated with a patient. The wearable device can further include a power source (e.g., a stored power device and/or battery), a power transmission component configured to transmit power and/or signal delivery parameters to the implantable device(s) 120, and one or more algorithms configured to control one or more aspects of the operation of the wearable device 101. Individual ones of the sensors can collect data associated with the patient, such as a patient's sleep state and/or respiratory performance. The one or more algorithms can be configured to adjust at least one of the signal delivery parameters based at least partially on the data collected by the sensors. In a representative embodiment, the wearable 101 can include an integrated sleep, respiratory diagnostics, and/or therapy modulation system configured to adjust or otherwise control one or more delivery parameters of the electrical signal delivered to the patient based on the collected sleep state and/or respiratory performance data, e.g., via one of more algorithms In some embodiments, the wearable device 101 can further include a cover or housing, at least a portion of which may be removeable, e.g., to expose an interior or interior portion of the wearable device 101. In these and other embodiments, the wearable device 101 cover can include fabric, or any other suitable material. Optionally, the wearable device 100 can include a reduced and/or simplified user interface configured to allow a user to interact with and/or otherwise control one or more of the elements of the wearable device 101 (e.g., check a charging status of the power source, adjust one or more of the signal delivery parameters, etc.).

The charger 121 for the wearable device 101 can be configured to supply power to the wearable device's 101 power source. The charger 121 can include a wireless (e.g., inductive) charger, a wired charger (e.g., wall-plug, charging cable, etc.), and/or any other suitable charger or charging device. Optionally, the charger 121 can include an integrated controller and/or a connected device, e.g., to control the charging of the wearable device 101 and/or to upload/download data to the wearable device 101 while the wearable device 101 is charging.

Individual ones of the one or more implantable devices 120 can include RFID (e.g., a unique RFID tag that can be used to identify and/or locate the associated implantable device 120a-n), an electrode receiver antenna (e.g., an RF power antenna), a power rectifier/DC-DC converter, circuitry (e.g., one or more application-specific integrated circuits (ASICs), a state machine, etc.), a signal generator, and two or more electrodes that are each individually selectable to deliver an electrical signal to a patient. The electrode receiver antenna can receive power from the power transmission component of the wearable device. The power rectifier/DC-DC converter can be operably coupled to the electrode receiver antenna, and can be configured to transmit the received power to the signal generator. Additionally, each of the implantable devices 120 can receive, via the electrode receiver antenna, information regarding one or more of the delivery parameters of the electrical signal to be generated by the signal generator and/or delivered to the patient via at least one of the electrodes of the implantable device(s) 120. The circuitry can include machine-readable instructions associated with the operation of the implantable device(s) 120. For example, the circuitry can include instructions that, when executed, can cause the signal generator to generate the electrical signal having the signal delivery parameter(s) received via the electrode receiver antenna. In these and other embodiments, the electrode receiver antenna can be used to transmit information associated with the implantable device 120 to the wearable device 101. For example, the implantable device 120 can transmit, to the wearable device 100 via the electrode receiver antenna, information associated with one or more of the signal delivery parameters of the electrical signal being applied to the patient. In these and other embodiments, individual ones of the one or more implantable devices 120 can include a hermetic package or housing configured such that the implantable device(s) 120 can be implanted within a patient.

Figure 3B:
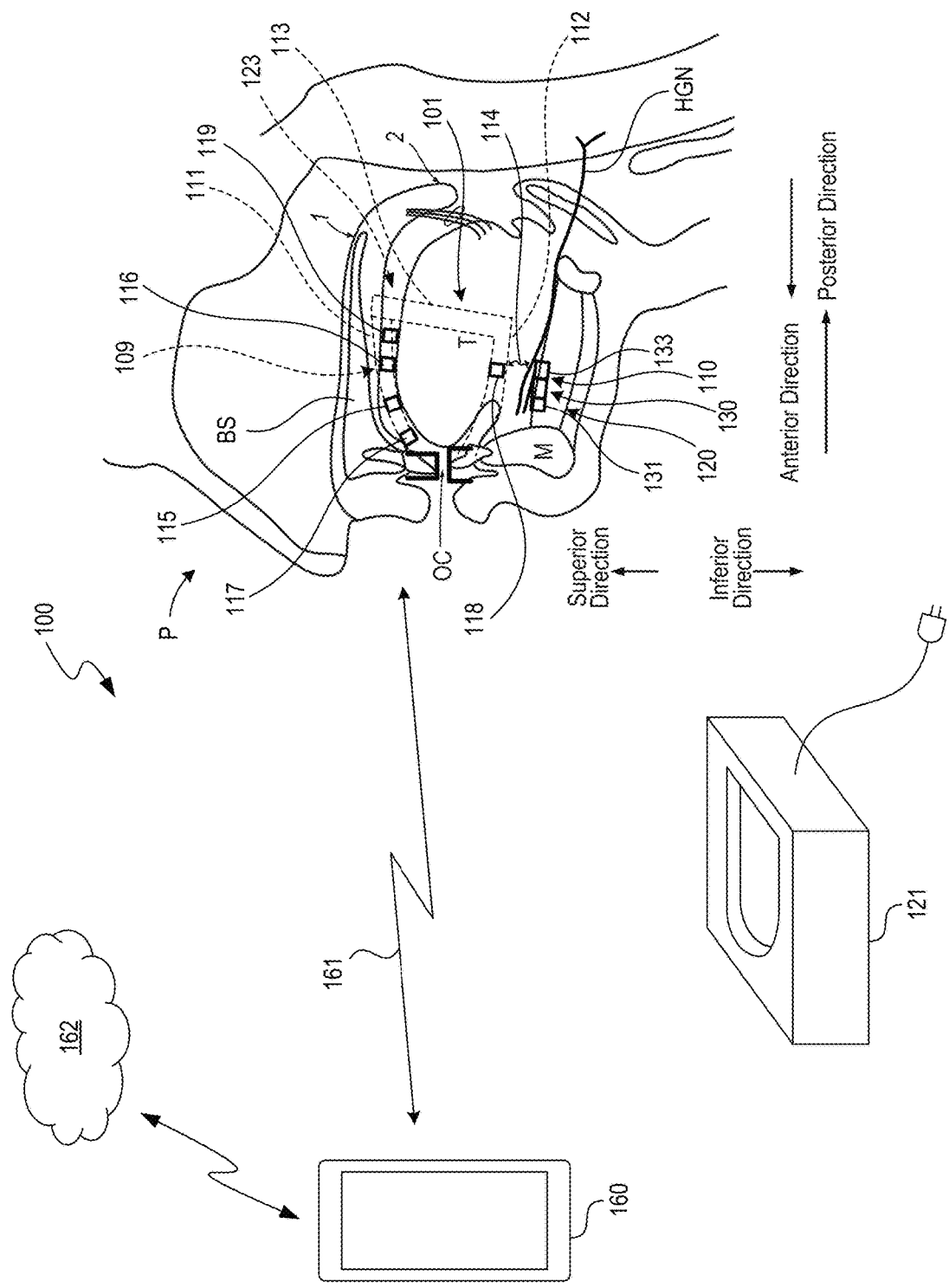
FIG. 3B is a partially schematic, side sectional view of a patient's upper airway, and elements of a system for treating sleeping disorders in accordance with embodiments of the present technology.

FIG. 3B is a partially schematic, isometric illustration of a representative implementation of the system 100 of FIG. 3A, shown in the context of the patient's anatomy, in a view similar to that described above with reference to FIG. 1. In a representative embodiment, the system 100 includes both implanted elements and external elements. The implanted elements can include the one or more implantable devices 120. Each implantable device 120 can include a signal delivery device 130 positioned adjacent to the target neural and/or muscle structure. The signal delivery device 130 can be secured in place with suture threads and/or other devices, e.g., anchors. The signal delivery device 130 is operatively coupled to a signal generator 110. In some embodiments, all the signal generation functions are performed by the implantable device 120, and in other embodiments, some signal generation functions may be performed by external elements. The signal generation functions and signal delivery functions may be performed by a single implantable device 120, or multiple devices.

The wearable device 101 can carry a power source 109. For purposes of illustration, the wearable device 101 is shown in FIG. 3B as including an intraoral device 123, e.g., a mouthpiece, that in turn carries the power source 109. As indicated above, the wearable device 101 can have other suitable configurations (e.g., collar, chinstrap, pillow, mattress overlay, among others) in other embodiments. The power source 109 provides power to a signal generator 110, which generates and directs signals (e.g., therapy signals) to one or more electrodes 131 carried by a signal delivery device 130. The signal delivery device 130 can be implanted at or proximate to the patient's hypoglossal nerve HGN using a minimally invasive technique, e.g., using a percutaneous injection needle. The power source 109 provides power to the signal generator 110 via a wireless power transmission link 114, for example, a midfield RF transmission link.

The signal generator 110 is typically controlled by the wearable device 101, which in turn can be controlled by the programmer 160 and/or any other suitable device, via a wireless programmer link 161. Accordingly, the patient P and/or a clinician can use the programmer 160 to direct the signal generator 110 (via the wearable device 101) to provide particular signals to particular electrodes, at particular times and/or in accordance with particular sequences. The programmer link 161 can be a two-way link, so that the programmer 160 (in addition to providing instructions to the wearable device 101 and/or the signal generator 110) can receive data regarding the therapy, the status of system components, and/or other suitable metrics. The data can be collected by one or more sensors 119 carried by the wearable device 101 (as shown schematically in FIG. 3B), and/or by the implantable device 120. In addition, the programmer 160 can communicate with the cloud 162 and/or other computer services to upload data received from the patient P, and/or download information to the wearable device 101 and/or the implantable device(s) 120. Downloaded data can include instructions and/or other data regarding suitable treatments (e.g., from other similarly-situated patients), updates for software executed on the circuitry carried by the wearable device 101 and/or the implantable device(s) 120, and/or other useful information. In other embodiments, the implantable device(s) 120 and/or the wearable device 101 include state machine components, which are not updatable. Representative data received from the patient can include respiratory rate, sleep state, wake state, heart rate, audio signals (corresponding to audible snoring, hypopnea events, and/or apnea events), body temperature, head orientation/position, saturated blood oxygen levels, air flow levels, thyroid movement, trachea movement, and/or tongue movement, photoplethysmography (PPG) data, among others. The data received from the patient can be generated by sensors 119 carried by the wearable device 101 and/or the implantable device 120. In a representative embodiment, the wearable device 101 performs executive functions, e.g., synthesizing information received from the programmer 160 and/or the sensors 119 to initiate, adjust and/or halt the therapy provided to the patient. The circuitry carried by the wearable device can accordingly include a controller programed with instructions to initiate, change, and/or halt the therapy delivered the implantable device, based on information received from the sensors. The received data can correspond to a measure of the patient's respiratory performance, sleep state, wake state, and/or other suitable metrics, for example, metrics that are used to rate the patient on the Apnea-Hypopnea Index (AHI).

In any of the foregoing embodiments, the wearable device 101 transmits power to the implantable devices 120 via the one or more power transmission links 112, and receives power (e.g., on an intermittent basis) from the charger 121. The charger 121 can accordingly include a conventional inductive coupling arrangement (e.g., Qi standard charging) and/or a conventional wired connection, as described previously and with reference to FIG. 3A.

In order to fit comfortably, the wearable device 101 (whether an intraoral device 123 or other type of wearable) can be custom-fit to the patient, or can be made available in different sizes, and/or can be partially configurable to fit individual patients. The intraoral device 123 is particularly suitable when the associated signal delivery device 130 is positioned at or proximate to target neural populations (e.g., the HGN) within the oral cavity. Whether the wearable device has a mouthpiece form factor or another suitable form factor, it can provide power to the implantable device 120, even if the implantable device is used to target neural populations other than, and/or in addition to, the HGN, e.g., branches of the vagus and/or ansa cervicalis nerves. In still further embodiments, the power source 109 can be mounted to the patient's skin via an adhesive, though it is expected that avoiding an adhesive will be more desirable/effective for the patient.

With reference to the specific embodiment shown in FIG. 3B, the intraoral device 123 can include both an upper mouthpiece portion 111, and a lower mouthpiece portion 112. The two mouthpiece portions 111, 112 can be coupled together via a connector 113. The connector 113 can provide a wired communication link between the two mouthpiece portions, and/or the connector 113 can mechanically position (and/or maintain the position of, or stabilize) the lower mouthpiece portion 112 relative to the upper mouthpiece portion 111. This approach can be used to, for example, advance the patient's lower jaw or mandible M relative to the patient's upper jaw, which is indicated by the bone structure BS in FIG. 3B. For example, embodiments of the present technology avoid or at least reduce jaw laxity (the patient's mouth hanging agape) using physical elements of the wearable device 101, in addition to the electrical stimulation powered by the wearable device. For example, a wearable device that includes a collar and/or chin strap can mechanically stabilize the patent's jaw in a target position.

The power source 109 can include one or more charge storage devices 116 (e.g., one or more batteries) that receive power from the charger 121 and store the power for transmission to the signal implantable device 120. Accordingly, the power source 109 can include circuitry 115 (e.g., first circuitry) that receives power from the charge storage device 116, conditions the power, and transmits the power to a power transmission antenna 118. The power transmission antenna 118 in turn transmits the power to the implantable device 120 via the wireless power transmission link 114 and an electrode receiver antenna 133 carried by the signal delivery device 130.

The intraoral device 123 can further include a data transceiver antenna 117 that receives data from the programmer 160, and/or transmits data to the programmer 160. Data transmitted to the programmer 160 can include sensor data obtained from one or more sensor(s) 119. Accordingly, the intraoral device 123 can carry the functional elements/components required to direct power to the signal delivery device 130, and can communicate with the programmer 160 so as to provide effective therapy for the patient. Further details of the signal delivery device 130 and the signal generator 110 are described below with reference to FIGS. 4-8B.

Figure 4:
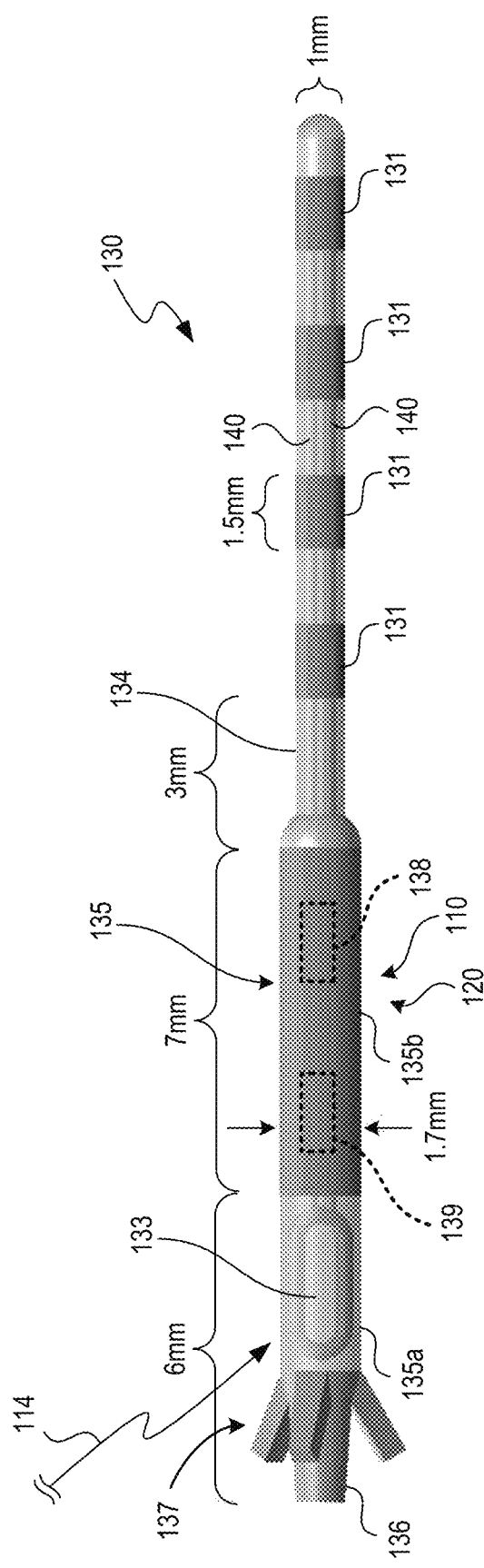
FIG. 4 is a partially schematic illustration of a signal delivery device configured in accordance with embodiments of the present technology.

FIG. 4 is a partially schematic side view of a signal delivery device 130 having elements configured in accordance with representative embodiments of the present technology. Representative dimensions are indicated in FIG. 4 to provide a sense of scale, but the technology is not limited by these dimensions unless expressly stated. The signal delivery device 130 includes a lead body 134, which can be generally flexible, and can carry one or more electrodes 131, which are generally rigid in some embodiments, and may be flexible in others. Flexible electrodes can increase the flexibility of the lead body generally to accommodate the tortuous anatomy/insertion path near the target nerve. For purposes of illustration, the lead body 134 is shown as carrying four electrodes 131 in FIG. 4, but in other embodiments, the lead body 134 can carry other suitable numbers of electrodes, for example, two electrodes 131. The electrodes 131 can be arranged in an array, for example, a one-dimensional linear array. The electrodes 131 can include conventional ring-shaped, or cylindrical electrodes, manufactured from a suitable, bio-compatible material, such as platinum/iridium, stainless steel, MP35N and/or or other suitable conductive implant materials. The electrodes 131 can each be connected to an individual conductor 140, for example, a thin wire filament, that extends through the lead body 134. Each electrode 131 can have a length of approximately 1.5 mm as shown in FIG. 4, or another suitable length in other embodiments. To provide a closed circuit, electrodes 131 are typically connected in (at least) pairs. A housing 135 and/or portions of the housing 135 can act as an electrode, e.g., a ground or return electrode.

The lead body 134 is connected to, and carried by, the housing 135, which in turn carries the signal generator 110 and circuit elements for receiving power. For example, the overall housing 135 can include an antenna housing or housing portion 135a and a circuit housing or housing portion 135b. The antenna housing 135a may be flexible, and can carry a receiver antenna 133 (or other suitable power reception device), which receives power from the wearable device 101 (FIGS. 3A and 3B) via the wireless transmission link 114. The circuit housing 135b can have the form of a generally cylindrical metallic "can" formed from titanium and/or another suitable material. The signal generator 110 can include a charge pump and/or DC-DC converter 139 and/or circuitry 138 (e.g., second circuitry) coupled to the receiver antenna 133. The circuitry 138 can include an ASIC, which can in turn include corresponding machine-readable instructions. The instructions can be updated wirelessly, using the electrode receiver antenna 133 for data transfer in addition to power transfer. For example, data can be transferred using pulse-width modulation (PWM) and/or other suitable techniques. Data can also be transferred in the opposite direction, e.g., using backscatter and/or other suitable techniques. For example the implantable device 120 can transmit a receipt to indicate that power has been received, and what magnitude the power is. This information can be used to autoregulate (up or down) the output of the signal generator 110, e.g., the transmitted signal and phase. Accordingly, the circuitry 138 can include a processor and memory, including pre-programmed and updatable instructions (e.g., in the form of an ASIC) for delivering therapy signals to the patient. For example, the system can include boot loader embedded firmware. Furthermore, the overall system can use RFID-type power transmission authorization to discriminate between multiple implantable devices, which may be powered by a single wearable device 101. RFID and/or other techniques can be used to implement security measures, e.g., to ensure that no foreign or unintended stimulation occurs. Such techniques can be implemented with suitable hardware/software carried by the implantable device 120, in at least some embodiments.

The overall housing 135 can further include a base 136, which is generally rigid, and one or more anchors 137. The anchor(s) 137 securely position the implantable device 120 relative to the patient's tissue. In a representative embodiment, the anchor 137 includes one or more tines that extend outwardly and into the patient's tissue when the implantable device 120 is injected or otherwise implanted in the patient. In other embodiments, the implantable device 120 can include other suitable anchors, and/or anchoring may occur at the distal and/or mid-section of the signal delivery device 130. Other suitable anchors include but are not limited to: (a) a bow spring that runs the longitudinal length of the electrode array and bows out to create fixation friction when the introducer sheath is withdrawn; (b) a small wire on a spring-loaded hinge that runs the longitudinal length of the electrodes array and bows out to create fixation friction when the introducer sheath is withdrawn; (c) a cam that, when rotated, expands in diameter to create frictional fixation when the corresponding push rod is rotated by the implanter; and/or (d) a torsion spring that, when rotated, expands in diameter to create frictional fixation when the push rod is rotated by the implanter.

To implant the implantable device 120, a practitioner uses a typical set of percutaneous implant tools, for example, an introducer, needle, cannula, and stylet, to position the implantable device 120 at the desired target location. In a particular example, the implantable device 120 is implanted percutaneously with a 3-4 Fr. needle. When the implantable device 120 is advanced from the cannula, the anchor 137 can deploy outwardly and secure the implantable device 120 in position. When the stylet is removed from the implantable device 120, for example, by withdrawing the stylet axially from an aperture in the base 136 and/or other portions of the housing 135, the implantable device 120 is in position to receive power and deliver therapy signals to the target nerve.

In operation, the receiver antenna 133 receives power wirelessly from the power source 109 carried by the associated wearable device 101 (FIGS. 3A and 3B, and described in further detail below with reference to FIGS. 5A-6). In at least some embodiments, the power received at the receiver antenna 133 is in a "midfield" range, for example, a radio frequency in a range of from about 300 MHz to about 6 GHz, e.g., about 600 MHz to about 2.45 GHz, or about 900 MHz to about 1.2 GHz. At this frequency, the useable range of the wireless power transmission link 114 is about 10 cm, more than enough to cover the distance between the implantable device 120 and the wearable device 101. At this range, the power transmission process is not expected to cause tissue heating, and accordingly provides an advantage over other power transmission techniques, for example, inductive transmission techniques. However, in embodiments for which the potential heating caused by inductive power transmission is adequately controlled, inductive techniques can be used in lieu of the midfield power transmission techniques described herein.

The AC power received at the receiver antenna 133 is rectified to DC, then transmitted to a DC-DC converter, charge pump, and/or transformer 139, and converted to pulses in a range from about 10 Hz to about 300 Hz. In other embodiments, the pulses can be delivered at a higher frequency (e.g., 10 kHz or more), and/or in the form of bursts. The amplitude of the signal can be from about 1 mV to about 5V (and in particular embodiments, 1 V to 2 V) in a voltage-controlled system, or from about 1 mA to about 6 mA in a current-controlled system. The circuitry 138 controls these signal delivery parameters, and transmits the resulting electrical signal to the electrodes 131 via the wire filaments or other conductors 140 within the lead body 134. Accordingly, the circuitry forms (at least part of) the signal generator 110 in that it receives power that is wirelessly transmitted to the implantable device 120, and generates the signal that is ultimately delivered to the patient. The electrical field(s) resulting from the currents transmitted by the electrodes 131 produces the desired effect (e.g., excitation and/or inhibition) at the target nerve. In at least some embodiments, the implantable device 120 need not include any on-board power storage elements (e.g., power capacitors and/or batteries), or any power storage elements having a storage capacity greater than 0.5 seconds, so as to reduce system volume. In other embodiments, the implantable device 120 can include one or more small charge storage devices (e.g., capacitors) that are compatible with the overall compact shape of the implantable device 120, and have a total charge storage capacity of no more than 1 second, 30 seconds, 1 minute, 2 minutes, or 5 minutes, depending on the embodiment.

In at least some embodiments, the electrical signal delivered to the patient can be delivered via a bipole formed by two of the electrodes 131. In other embodiments, the signal can be a monopolar signal, with the housing 135 (e.g., the circuit housing 135b) forming a ground or return electrode. In general, the waveform includes a biphasic, charge balanced waveform, as will be discussed in greater detail below with reference to FIGS. 8A and 8B.

Figure 5A:
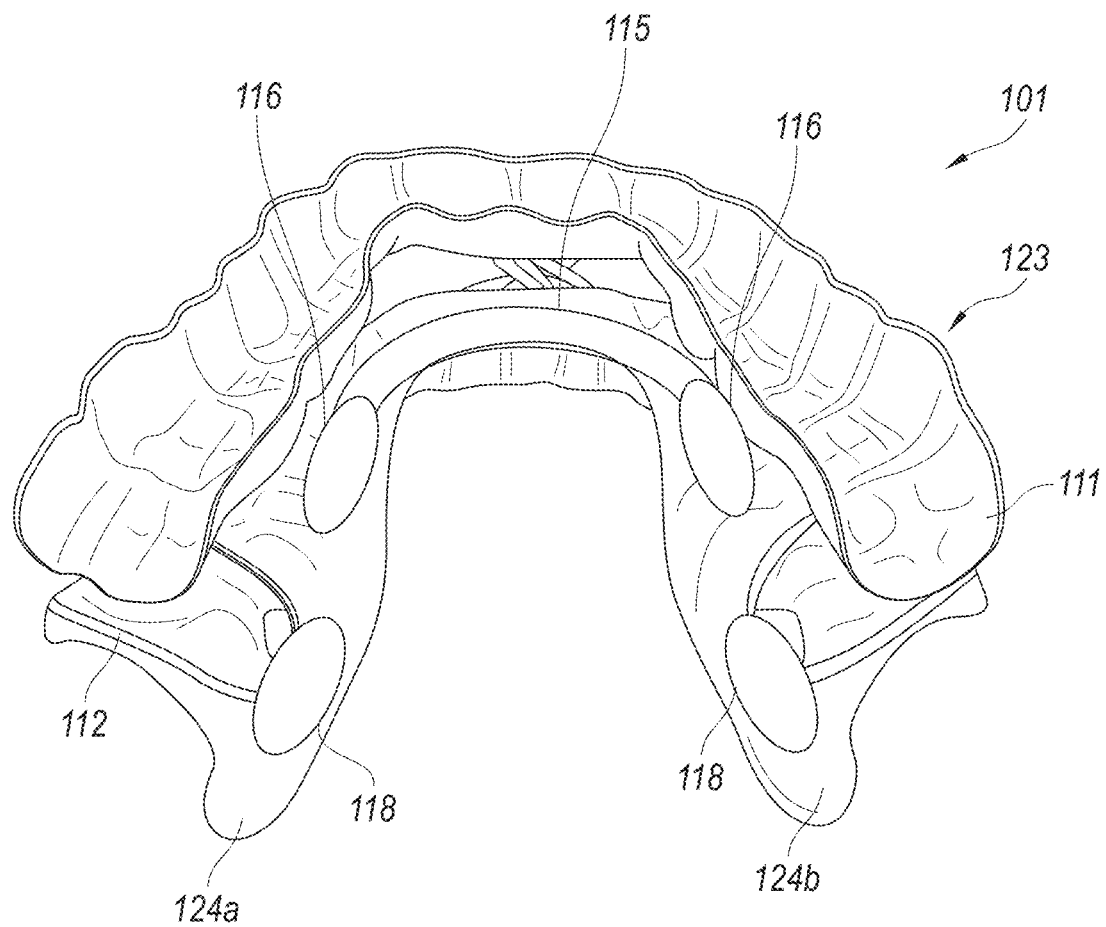
FIG. 5A is a partially schematic illustration of a signal generator having an upper mouthpiece portion, a lower mouthpiece portion, and a circuit and power supply positioned at an inner surface of the lower mouthpiece portion.
Figure 5B:
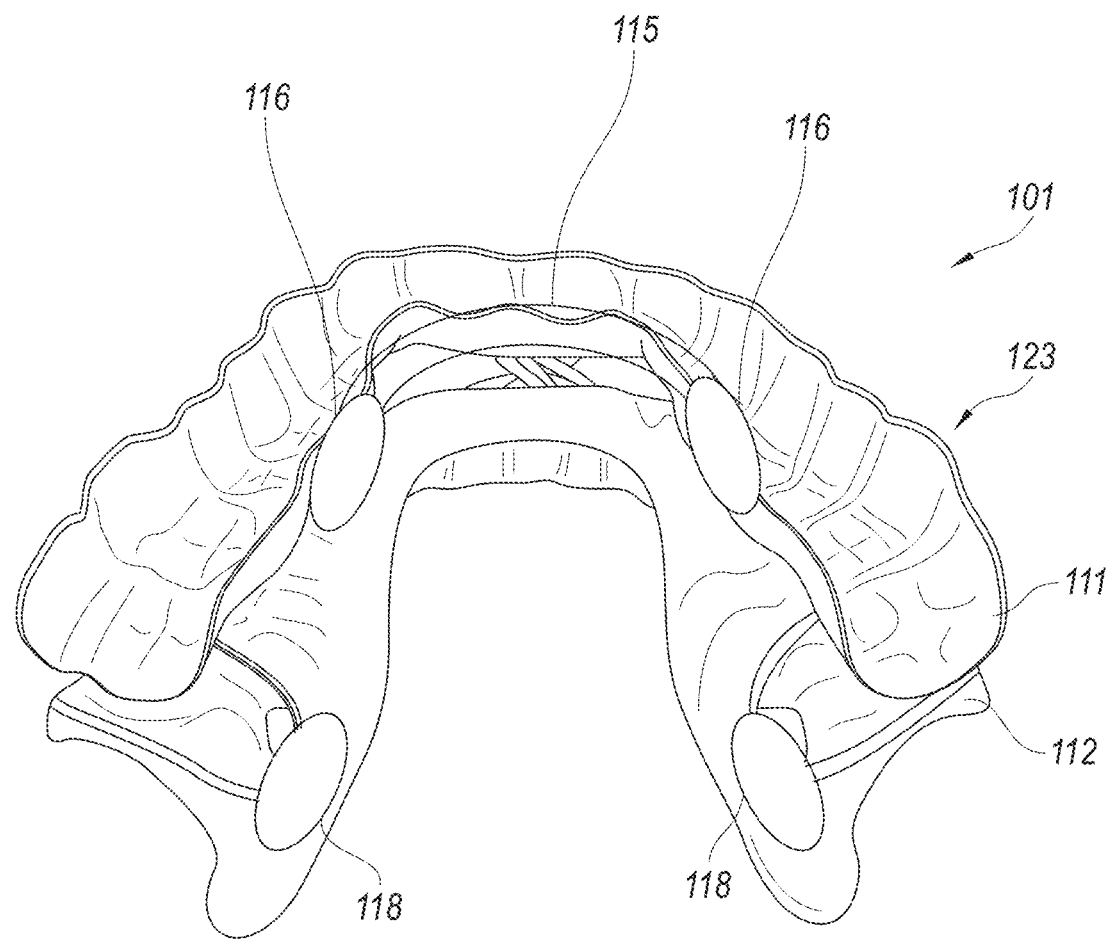
FIG. 5B is a partially schematic illustration of a signal generator having an upper mouthpiece portion, a lower mouthpiece portion, and a circuit and power supply positioned at an inner surface of the upper mouthpiece portion.
Figure 5C:
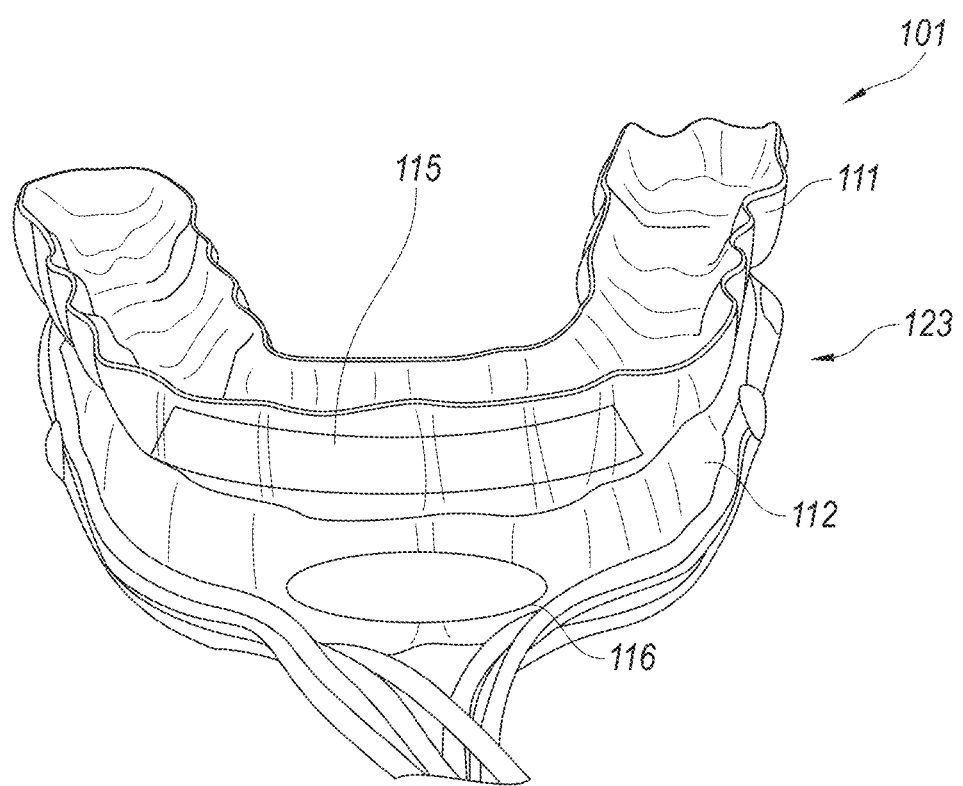
FIG. 5C is a partially schematic illustration of a signal generator having an upper mouthpiece portion, a lower mouthpiece portion, and a circuit and power supply positioned at an outer surface of the upper and/or lower mouthpiece portions.
Figure 6:
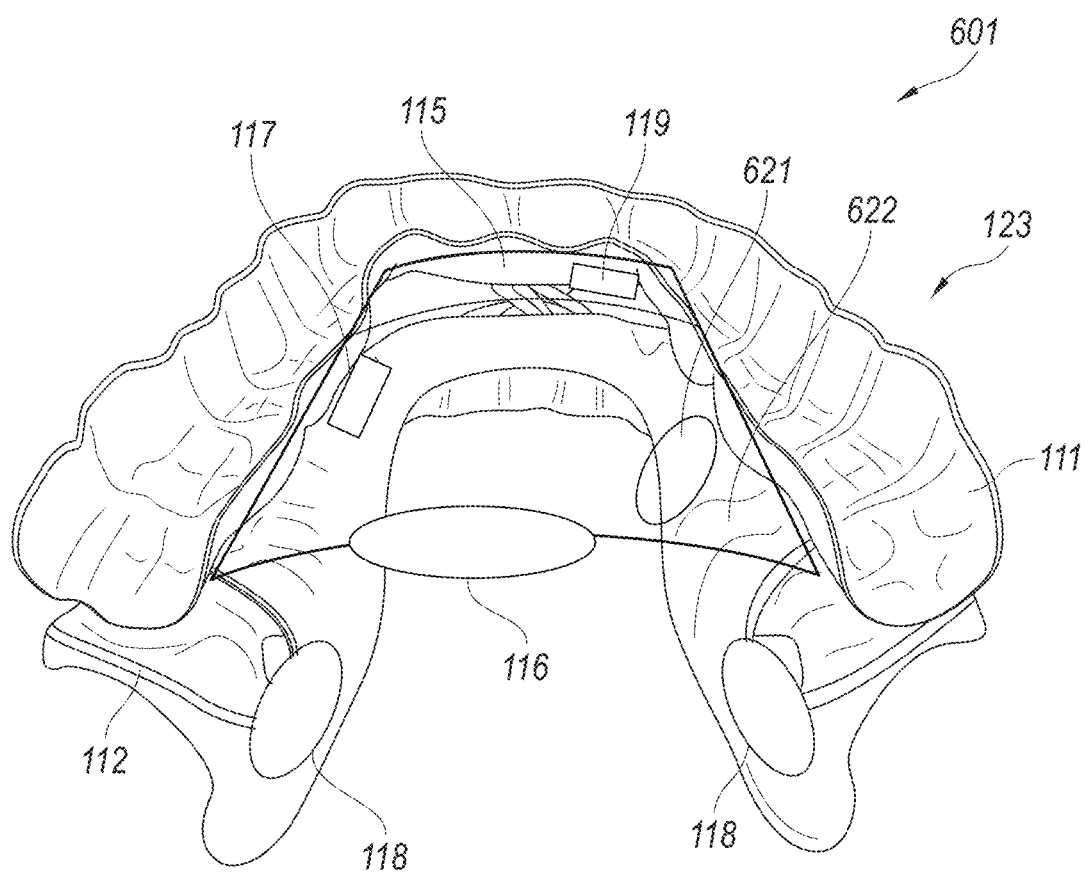
FIG. 6 is a partially schematic, isometric illustration of a signal delivery device having an upper mouthpiece portion with a roof portion carrying circuitry, a power supply, one or more sensors, and/or a data transceiver antenna, in accordance with representative embodiments of the present technology.

FIGS. 5A-6 illustrate wearable devices 101 configured to supply power to the implantable device 120, in accordance with representative embodiments of the present technology. Referring first to FIG. 5A, a representative wearable device 101 includes an intraoral device 123 having an upper mouthpiece portion 111 and a lower mouthpiece portion 112. The lower mouthpiece portion 112 includes one or more transmission antennas 118 that direct power to the implantable device 120, described above with reference to FIG. 4. In a representative embodiment, the patient has two implantable devices 120 implanted bilaterally, that is, at each of the patient's two hypoglossal nerves, one located on the right side of the patient's oral cavity, and the other located on the left. Accordingly, the intraoral device 123 can include two power transmission antennas 118, each positioned to direct power to one of the implantable device 120. In an embodiment shown in FIG. 5A, the lower mouthpiece portion 112 includes two corresponding extensions 124, illustrated as a left extension 124a, and a right extension 124b. Each extension 124 houses one of the transmission antennas 118, and is positioned to locate the transmission antenna 118 close to the corresponding implantable device 120, in a manner that remains comfortable for the patient when the patient wears the intraoral device 123.

The intraoral device 123 also includes one or more power supplies 116 coupled to circuitry 115 that directs power to the transmission antennas 118. The power supply 116 can include one or more batteries, capacitors, and/or other charge storage devices configured to store enough energy to supply the signal delivery device(s) for a suitable therapy period. A suitable therapy period typically includes at least four hours in some embodiments, and at least one night in other embodiments. The circuitry 115 receives current from the power supply 116 and converts the current to a suitable midfield radio frequency. The current is directed to the transmission antenna(s) 118. In an embodiment shown in FIG. 5A, the circuitry 115 and power supply 116 are carried by the lower mouthpiece portion 112, and are positioned along the outer surfaces of the lower mouthpiece portion 112, so as to face toward the patient's lower lip. With this arrangement, the electrical elements are not expected to interfere with the anterior motion of the patient's tongue. In another embodiment, for example, as shown in FIG. 5B, the circuitry 115 and the power supply 116 can be carried by the upper mouthpiece portion 111. In this embodiment, the circuitry 115 and power supply 116 are positioned along the inner surfaces of the upper mouthpiece portion 111 so as to face toward the interior of the patient's oral cavity rather than toward the patient's lips. Because the electrical elements are on the upper mouthpiece portion 111, they are not expected to interfere with the anterior motion of the patient's tongue, even though they face toward the interior of the patient's oral cavity. The circuitry 115 directs electrical current to the antenna(s) via one or more wires (not shown in FIG. 5A) that pass through a corresponding connector 113 (shown in FIG. 3B) coupled between the upper mouthpiece portion 111 and the lower mouthpiece portion 112.

FIG. 5C illustrates a further representative embodiment in which the wearable device 101 includes circuitry 115 carried by the upper mouthpiece portion 111, and a power supply 116 carried by the lower mouthpiece portion 112. In this case, a communication link carried by the connector 113 (FIG. 3B) transmits current from the power supply 116 to the circuitry 115, and then transmits current from the circuitry 115 to the transmission antenna(s) 118 (not visible in FIG. 5C).

FIG. 6 is a partially schematic, isometric illustration of a wearable device 601 configured in accordance with still further embodiments of the present technology. The upper mouthpiece portion 111 includes a roof portion 622 extending transversely from one side of the upper mouthpiece portion 111 to the other, so as to be positioned upwardly against the roof of the patient's mouth. Several of the elements of the wearable device 101 can accordingly be carried by the roof portion 622. Such elements can include the circuitry 115, the power supply 116, the data transceiver antenna 117 (described above with reference to FIG. 3B), a charging coil 621 (for recharging the power supply 116 via the charger 121, shown in FIGS. 3A and 3B), and one or more sensors 119 (also discussed above with reference to FIGS. 3A and 3B). Accordingly, the roof portion 622 can provide additional volume in which to carry the foregoing elements of the wearable device 101. Sensors 119, for example, can include but are not limited to, temperature sensors such as thermistors and/or thermocouples, sound sensors, vibration sensors, pressure sensors, force sensors, strain gauges, magnetometers, accelerometers, gyroscopes, impedance sensors, EMG sensors, gas sensors and/or chemical sensors, oxygen saturation sensors, photoplethysmography sensors, flow sensors (oral- or nasal-manometry), and/or other sensors that can sense conditions or characteristics (e.g., sleep state, wake state) of the patient. In some representative embodiments, the patient's respiration parameters can be used to trigger stimulation based on the patient's breathing cycle as well as information that may indicate an apnea event is occurring or is likely to occur. In a particular embodiment, the overall system includes a pulse oximeter, a photoplethysmography sensor, and at least one patient orientation sensor to provide suitable patient feedback on which to base system actions.

Any of the foregoing components described with reference to FIGS. 5A-6 can be positioned along the outer surfaces of the mouthpiece portion(s), or in other embodiments, these components can face inwardly, rather than outwardly, from the mouthpiece portions. As indicated above, an advantage of the components being on the outer surface of the mouthpiece is that the components would not impinge on the space occupied by the tongue as it protrudes forward during stimulation. In at least some embodiments, the battery can be positioned so that it can be readily removed and replaced.

Figure 7:
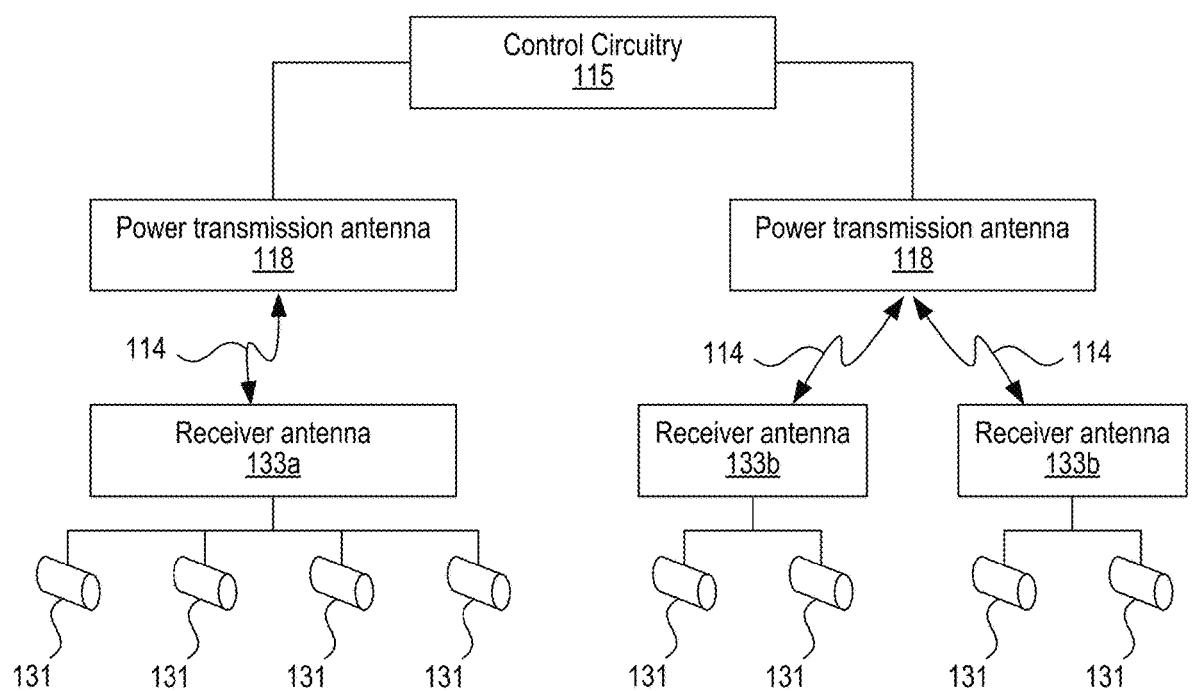
FIG. 7 is a partially schematic illustration of multiple arrangements for controlling individual electrodes with control circuitry, in accordance with embodiments of the present technology.

FIG. 7 is a schematic illustration of an arrangement for controlling the electrical signals applied to the patient, in accordance with representative embodiments of the present technology. In general, the control circuitry 115 provides current to one or more power transmission antennas 118, which in turn direct the power to corresponding electrode receiver antennas 133, via corresponding wireless power transmission links 114.

For purposes of illustration, FIG. 7 illustrates two control arrangements on a single device: one for the left side of the patient's oral cavity and one for the right. This is one possible organization, and in other embodiments, the same arrangement is used for both left and right sides. As shown in FIG. 7, a first receiver antenna 133*a* can provide signals to each of four corresponding electrodes 131. Two second receiver antennas 133*b* can each provide power to two electrodes 131. The implemented arrangement can be selected based on the utility associated with controlling individual electrodes via corresponding receiver antennas. For example, the first receiver antenna 133*a* can deliver the same signal, simultaneously, to multiple electrodes 131 (and/or pairs of electrodes 131) connected to it. On the other hand, the second receiver antennas 133*b* can each deliver signals independently to the corresponding electrodes to which they are coupled. This can allow the second receiver antennas 133*b* to sequence the signals applied to the corresponding electrodes 131. In some embodiments, this arrangement can advantageously allow the practitioner to direct one signal to one portion of the hypoglossal nerve at one point in time, and the same or another signal to another portion of the hypoglossal nerve, or another nerve, at another point in time. It is expected that the ability to control both spatial and temporal aspects of the signals delivered to the target nerve, or nerves, can improve the efficacy with which the device reduces the patient's obstructive sleep apnea (OSA). For example, the signals may be delivered to different portions of the hypoglossal nerve, and/or to other nerves, including the ansa cervicalis (e.g., to promote caudal movement of the pharynx), and/or the vagal nerve, as its branches activate many muscles of the upper airway including the motor muscles of the larynx and the palatoglossus.

More generally, the multiple injectable electrodes 131 can be wirelessly activated by the remotely positioned wearable device, in a phased manner (e.g., with millisecond-range timing offsets) to sequence contractions of the corresponding muscles and thereby address the patient's sleeping disorder(s). In addition, the system has the flexibility to change the target neuron(s) to which the signal is directed, in combination with the certainty and robustness provided by an implanted signal delivery device.

In at least some embodiments, the control circuitry 115 controls both of the power transmission antennas 118, and therefore provides overall control of the signals delivered to the patient. In other embodiments, the authority to control one or more antenna(s) 118 and/or corresponding electrodes 131 can be distributed. For example, one element of the control circuitry can control one power transmission antenna 118 and another can control the other power transmission antenna 118. The control authority can be further distributed among different receiver antenna(s) 133, as shown in FIG. 7. In any of these embodiments, when control is distributed below the high level control circuitry 115, the system includes provisions that allow for communication between individual controller elements so as to keep all the control elements synchronized.

4. Representative Waveforms

Figure 8A:
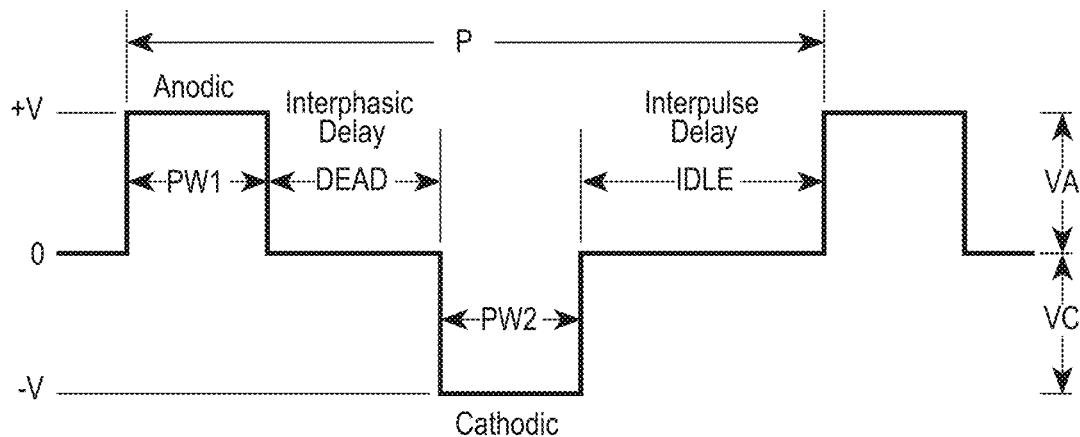
FIG. 8A is a representative example of a waveform having waveform parameters selected in accordance with embodiments of the present technology.
Figure 8B:
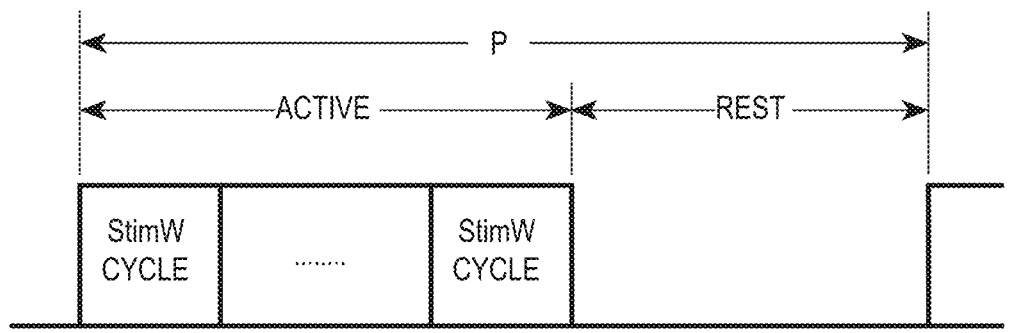
FIG. 8B is a representative example of a waveform having active and resting periods in accordance with embodiments of the present technology.

The signal generators and delivery devices described above can generate and deliver any of a variety of suitable electrical stimulation waveforms a to modulate the actions of the patient's neurons and/or muscles. Representative examples are illustrated in FIGS. 8A and 8B and include a series of a biphasic stimulation pulses that form stimulation wave cycles having a period as identified in FIGS. 8A and 8B. The waveform parameters can include active cycles and rest cycles. Each period P includes one or more pulses. The waveform shown in FIG. 8A comprises an anodic pulse followed by an interphasic delay, a cathodic pulse and then an interpulse delay. Accordingly, the overall period P or cycle includes the following parameters: anodic pulse width (PW1), anodic amplitude (e.g., voltage or current amplitude VA), interphasic delay/dead time, cathodic pulse width (PW2), cathodic amplitude (e.g., voltage or current amplitude VC), interpulse delay/idle time, and peak-to-peak amplitude (PP). The parameters may also include the identity of the electrode(s) to which the signal is directed. The anodic pulse width (PW1) in some representative embodiments is between 30 μs and 300 μs. The anodic amplitude (VA) and cathodic amplitude (VC) in some representative embodiments ranges from 1 mV to 5 V, or 1 mA to 6 mA. The interphasic delay in some representative embodiments can be from 10 μs to 100 μs. The cathodic pulse width (PW1) is some representative embodiments is between 30 μs and 300 μs. In representative embodiments, the anodic and cathodic phases are charge balanced, though the phases need not be symmetrically shaped. The interpulse delay in some representative embodiments can be from 10 μs to 100 μs. The peak-to-peak amplitude in some representative embodiments can be from about 2 mA to 12 mA. Representative frequencies range from about 10 Hz to about 300 Hz in some embodiments, and up to 100 kHz (e.g., 10 kHz) in others. The pulses can be delivered continuously or in bursts.

FIG. 8B illustrates a representative waveform comprising an active portion and a rest portion. The active portion includes one or more periods having the characteristics described above with reference to FIG. 8A. The rest portion has no stimulation pulses. According to some representative embodiments, the ratio of active portion to rest portion can be between 1:1 and 1:9. As a representative example, if the ratio is 1:9, and there are 300 active periods, there can be 2700 rest portions.

In a representative example, the stimulation voltage may be presented independently to each contact or electrode. For the positive pulse, the positive contact can be pulled to the drive voltage and the negative contact is pulled to ground. For the negative pulse, the negative contact can be pulled to the drive voltage and the positive contact is pulled to ground. For dead time and idle time, both contacts are driven to ground. For the rest time, both contacts are at a high impedance. To prevent DC current in the contacts, each half-bridge can be coupled to the contact through a capacitor, for example, a 100 μF capacitor. In addition, a resistor can be placed in series with each capacitor to limit the current in the case of a shorted contact. The pulses of the therapeutic waveform cycle may or may not be symmetric, but, are generally shaped to provide a net-zero charge across the contacts, e.g., to provide charge balancing.

From the foregoing, it will be appreciated that specific embodiments of the disclosed technology have been described herein for purposes of illustration, but that various modifications may be made without deviating from the technology. For example, the power source and associated wearable can have configurations other than an intraoral mouthpiece, that also deliver power wirelessly to one or more implanted electrodes. Representative configurations include external, skin-mounted devices, and devices that are worn around the patient's neck, which may be suitable for targeting the ansa cervicalis, vagal nerve, and/or other nerves other than the HGN. Other representative targets for the stimulation include palatoglossal stimulation, cranial nerve stimulation, direct palatoglossus muscle stimulation, hyolaryngeal stimulation, and/or glossopharyngeal nerve stimulation. The anchor used to secure the signal delivery device in place can have configurations other than deployable tines, including s-curve elements, helixes, and/or porous structures that promote tissue in-growth. The signal delivery device was described above as including multiple housings that form an overall housing. In other embodiments, the multiple housing can be portions of a unitary overall housing. The functions performed by the overall system can be divided among the system elements (e.g., the programmer, wearable device, and implantable device) in manners other than those expressly shown and described herein.

Certain aspects of the technology described in the context of particular embodiments may be combined or eliminated in other embodiments. For example, signal delivery devices having any of a variety of suitable configurations can be used with any one signal generator, and signal generators having any of a variety of suitable configurations can be used with any one signal delivery device. Further, while advantages associated with certain embodiments of the disclosed technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

As used herein, the phrase "and/or," as in "A" and/or "B" refers to A alone, B alone and both A and B. To the extent any materials incorporated herein by reference conflict with the present disclosure, the present disclosure controls. As used herein, the terms "about," "approximately," and similar terms of approximation refer to values within 10% of the stated value.

The following examples provide additional representative features of the present technology.

EXAMPLES

1. A patient treatment system, comprising:
   a wearable device carrying:
   a power storage device;
   a power transmission antenna coupled to the power storage device and configured to emit an RF signal in a frequency range of 300 MHz to 6 GHz; and
   first control circuitry coupled between the power storage device and the power transmission antenna; and
   an implantable device having:
   an electrode;
   a housing carrying the electrode;
   an anchor carried by the housing and positioned to secure the implantable device to tissue in a patient's oral cavity;
   an electrode receiver antenna configured to receive an RF signal in a frequency range of 300 MHz to 6 GHz;
   a signal generator coupled to the electrode receiver antenna and the electrode to direct a signal to the electrode at a frequency in a range of 10 Hz to 300 Hz; and
   second circuitry coupled between the signal generator and the electrode to control the delivery of the signal to the electrode.

2. The system of example 1, wherein the implantable device is needle-deliverable device, and wherein the electrodes are positioned to be implanted proximate to a patient's hypoglossal nerve and/or ansa cervicalis, and wherein the system further comprises:
   at least one sensor carried by the wearable device or the implantable device, the at least one sensor being configured to detect a characteristic of the patient's respiratory performance; and
   a controller carried by the wearable device and programmed with instructions that, when executed, initiate, change, and/or halt the delivery of the signal to the electrode, based at least in part on information received from the at least one sensor.

3. The system of example 2 wherein the at least one sensor includes a pulse oximeter, a photoplethysmography sensor, and a patient orientation sensor.

4. The system of any of examples 1-3 wherein the implantable device does not include a charge storage element.

5. The system of any of examples 1-4 wherein the electrode is a first electrode, and wherein the implantable device includes a second electrode, and wherein at least one of the first circuitry or the second circuitry include instructions that, when executed, direct signals to the first and second electrodes that are sequenced, with the first electrode delivering a first signal to the patient at a first point in time, and the second electrode delivering a second signal to the patient at a second point in time.

6. The system of any of examples 1-4 wherein the wearable device includes an intraoral device configured to be positioned within the patient's oral cavity.

7. The system of example 6 wherein at least a first portion of the intraoral device is shaped to conform to at least a second portion of the patient's oral cavity.

8. The system of example 6 wherein the intraoral device includes an upper mouthpiece portion, a lower mouthpiece portion and a connector coupling the upper and lower mouthpiece portions.

9. The system of example 8 wherein the lower mouthpiece portion is movable relative to the upper mouthpiece portion to advance the patient's mandible.

10. The system of example 8 wherein the lower mouthpiece portion carries the power transmission antenna, the charge storage device, and the first circuitry.

11. The system of example 8 wherein the lower mouthpiece portion carries the power transmission antenna and the upper mouthpiece portion carries the charge storage device and the first circuitry.

12. The system of example 11 wherein the upper mouthpiece portion includes a roof portion that carries the charge storage device or the first circuitry.

13. The system of example 8 wherein the lower mouthpiece portion carries the power storage device, the upper mouthpiece portion carries the first circuitry, and the connector includes a communication link to transmit power from the power supply to the circuitry.

14. The system of example 8 wherein at least at least a part of the lower mouthpiece portion is shaped to conform to a lower region of the patient's oral cavity.

15. The system of example 8 wherein at least a part of the upper mouthpiece portion is shaped to conform to an upper region of the patient's oral cavity.

16. The system of any of examples 1-15 wherein (i) the implantable device is a first implantable device positioned on a first side of the patient's oral cavity and (ii) the electrode is a first electrode, the system further comprising a second implantable device positioned on a second side of the patient oral cavity opposite the first implantable device, the second implantable device including a second electrode.

17. The system of any of examples 1-5 wherein the wearable device includes at least one of a neck collar, a chinstrap, a pillow, and/or a mattress overlay.

18. The system of any of examples 1-17 wherein at least one of the first circuitry or the second circuitry include instructions that, when executed, cause the electrode to deliver a signal to the patient, wherein the signal includes at least one of:
   a pulse width between 30 us and 300 us;
   an anodic amplitude between 1 mA and 6 mA or between 1 mV and 5 V; and
   a cathodic amplitude between 1 mA and 6 mA or between 1 mV and 5 V.

19. The system of example 1 wherein the wearable device further includes at least one sensor positioned to detect at least one physiological parameter of the patient, the at least one physiological parameter including at least one of a respiratory rate, a heart rate, an audio signal, a body temperature, a head position, a saturated blood oxygen level, an air flow level, movement of the patient's larynx, and/or movement of the patient's tongue.

20. An sleep apnea treatment system, comprising:
   an intraoral device configured to fit within a patient's oral cavity, the intraoral device including—
   a lower mouthpiece portion carrying a power transmission antenna configured to emit an RF signal at a first frequency, and
   an upper mouthpiece portion opposite the lower mouthpiece portion, the upper mouthpiece portion carrying—
   a power storage device operably coupled to the power transmission antenna, and
   first control circuitry operably coupled to the power storage device and the power transmission antenna; and a connector coupling the lower portion and the upper portion; and an implantable device having:
  an electrode,
  an electrode receiver antenna configured to receive the RF signal emitted by the power transmission antenna,
  a signal generator coupled to the electrode receiver antenna and the electrode and operable to direct a stimulus signal to the electrode at a second frequency, and
  second circuitry coupled between the signal generator and the electrode to control the delivery of the stimulus signal to the electrode.

21. The sleep apnea treatment system of example 20 wherein the implantable device does not include a charge storage element.

22. The sleep apnea treatment system of any of examples 20-21 wherein the electrode is a first electrode, and wherein the implantable device includes a second electrode, and wherein at least one of the first circuitry or the second circuitry include instructions that, when executed, direct signals to the first and second electrodes that are sequenced, with the first electrode delivering a signal to the patient at a first point in time, and the second electrode delivering a signal to the patient at a second point in time.

23. A method of directing an electrical signal to a person, comprising:
  programming a wearable device to transmit, via a power transmission antenna of the wearable device positioned to be in wireless communication with a receiver antenna of an implantable device, a first electrical signal, at least a portion of the first electrical signal having a first frequency in a first frequency range from about 300 MHz to about 6 GHz; and
  programming a pulse generator of the implantable device to—
    receive, via the electrode receiver antenna, the first electrical signal; and
    deliver, via at least one electrode of the implantable device positioned to be in electrical communication with a target nerve of the person, a second electrical signal, at least a portion of the second electrical signal having a second frequency in a second frequency range of up to 100 kHz.

24. The method of example 23 wherein the first frequency range is from about 900 MHz to about 1.2 GHz.

25. The method of any of examples 23-24 wherein the second frequency range is from about 10 Hz to about 300 Hz.

26. The method of any of examples 23-25 wherein the portion of the second electrical signal further includes an anodic amplitude in an anodic amplitude range from 1 mV to 5V or from 1 mA to 6 mA 27. The method of any of examples 23-26 wherein the portion of the second electrical further includes an interphase delay in an interphase delay range from 10 μs to 100 μs.

28. The method of any of examples 23-27 wherein the portion of the second electrical signal further includes an interpulse delay in an interpulse delay range from 10 μs to 100 μs.

29. The method any of examples 23-28 wherein the portion of the second electrical signal further includes a peak-to-peak amplitude in a peak-to-peak amplitude range from 2 mA to 12 mA.

30. The method of any of examples 23-29 wherein the person has sleep apnea.

31. The method of example any of examples 23-30 wherein programming the pulse generator includes programming the pulse generator to deliver the second electrical signal over a therapy period.

32. The method of example 31 wherein the therapy period lasts at least four hours.

33. The method of example 31 wherein the therapy period includes at least one active portion and at least one rest portion.

34. A method of treating a patient, comprising:
  percutaneously implanting an implantable device proximate a medial branch of the patient's hypoglossal nerve such that an electrode carried by the implantable device is positioned to be in electrical communication with the medial branch of the patient's hypoglossal nerve;
  transmitting a first signal from a power transmission antenna of a wearable device to a receiver antenna of the implantable device;
  converting, via a signal generator of the implantable device, the first signal into a second signal; and
  applying, via the electrode, the second signal to the medial branch of the patient's hypoglossal nerve.

35. The method of example 34 wherein transmitting the first signal includes transmitting the first signal in a frequency range from about 300 MHz to about 6 GHz.

36. The method of any of examples 34-35 wherein transmitting the second signal includes transmitting the second signal in a frequency range of up to 100 kHz.

37. The method of any of examples 34-36 wherein transmitting the second signal includes transmitting the second signal in a frequency range from about 10 Hz to about 300 Hz.

38. The method of any of examples 34-37 wherein the electrode is a first electrode, and wherein applying the second signal includes:
  applying, via the first electrode, a first portion of the second signal at a first point in time; and
  applying, via the second electrode, a second portion of the second signal at a second point in time;

39. The method of any of examples 34-38 wherein the implantable device is a first implantable device and the electrode is a first electrode, the method further comprising:
  percutaneously implanting a second implantable device such that a second electrode carried by the second implantable device is positioned to be in electrical communication with at least a portion of the patient's hypoglossal nerve, ansa cervicalis nerve, vagal nerve, glossopharyngeal nerve, palatoglossus muscle, or hyolaryngeal complex.

40. The method of example 39 wherein:
  implanting the first implantable device include implanting the first implantable device on a first side of the patient's oral cavity; and
  implanting the second implantable device includes implanting the second implantable device on a second side of the patient's oral cavity.

We claim:

1. A method of treating a patient, comprising:
  providing power to
    a first signal generator of a first percutaneously injectable device, the first percutaneously injectable device further including a first signal delivery device operably coupled to the first signal generator and positioned to deliver a first electrical signal to a hypoglossal nerve of the patient; and a second signal generator of a second percutaneously injectable device, the second percutaneously injectable device further including a second signal delivery device operably coupled to the second signal generator and positioned to deliver a second electrical signal to an ansa cervicalis nerve of the patient;

delivering, via the first signal delivery device, the first electrical signal to the patient's hypoglossal nerve; and delivering, via the second signal delivery device, the second electrical signal to the patient's ansa cervicalis nerve.

2. The method of claim 1 wherein providing the power includes:

wirelessly providing a first power signal to the first signal generator; and wirelessly providing a second power signal to the second signal generator.

3. The method of claim 1 wherein providing the power includes:

providing a first power signal to the first signal generator from a first charge storage device of the first percutaneously injectable device; and providing a second power signal to the second signal generator from a second charge storage device of the second percutaneously injectable device.

4. The method of claim 3 wherein the first charge storage device and/or the second charge storage device have a total charge storage capacity of no more than 5 minutes.

5. The method of claim 1, further comprising:

percutaneously injecting the first percutaneously injectable device such that the first signal delivery device is positioned to deliver the first electrical signal to the patient's hypoglossal nerve; and percutaneously injecting the second percutaneously injectable device such that the second signal delivery device is positioned to deliver the second electrical signal to the patient's ansa cervicalis nerve.

6. The method of claim 1 wherein providing the power includes transmitting one or more power signals, via one or more external power transmission devices, a first power receiving device of the first percutaneously injectable device and/or to a second power receiving device of the second percutaneously injectable device.

7. The method of claim 6 wherein transmitting the one or more power signals includes:

transmitting, via a first external power transmission device, a first power signal to the first power receiving device; and transmitting, via a second external power transmission device, a second power signal to the second power receiving device.

8. The method of claim 1 wherein providing the power includes providing power via an inductive coil or an RF antenna.

9. The method of claim 1 wherein:

the first signal delivery device includes a first lead body carrying one or more first electrodes; and the second signal delivery device includes a second lead body carrying one or more second electrodes.

10. A method of treating a breathing disorder in a patient, comprising:

providing power to a first signal generator of a first percutaneously injectable device, the first percutaneously injectable device further including a first signal delivery device operably coupled to the first signal generator and positioned to deliver a first electrical signal to a hypoglossal nerve of the patient; and a second signal generator of a second percutaneously injectable device, the second percutaneously injectable device further including a second signal delivery device operably coupled to the second signal generator and positioned to deliver a second electrical signal to an ansa cervicalis nerve of the patient; and in response to an indication that the patient is experiencing apnea and/or hypopnea delivering, via the first signal delivery device, the first electrical signal to the patient's hypoglossal nerve; and/or delivering, via the second signal delivery device, the second electrical signal to the patient's ansa cervicalis nerve.

11. The method of claim 10 wherein providing the power includes:

transmitting, via a first power transmission device, a first power signal to the first signal generator via a first power receiving device of the first percutaneously injectable device; and transmitting, via a second power transmission device, a second power signal to the second signal generator via a second power receiving device of the second percutaneously injectable device.

12. The method of claim 10 wherein providing the power includes providing power via one or more inductive coils and/or one or more RF antennas.

13. The method of claim 10 wherein providing the power includes:

providing a first power signal to the first signal generator via a first charge storage device of the first percutaneously injectable device; and providing a second power signal to the second signal generator via a second charge storage device of the second percutaneously injectable device.

14. The method of claim 13 wherein the first charge storage device and/or the second charge storage device have a total charge storage capacity of no more than 5 minutes.

15. The method of claim 10 wherein the indication includes information associated with the patient's respiratory rate and/or audio signals associated with one or more apnea and/or hypopnea events.

16. The method of claim 10 wherein the indication includes information obtained via a flow sensor, a pulse oximeter, a photoplethysmography sensor, and/or a patient orientation sensor.

17. The method of claim 10, further comprising:

percutaneously injecting the first percutaneously injectable device such that the first signal delivery device is positioned to deliver the first electrical signal to the patient's hypoglossal nerve; and percutaneously injecting the second percutaneously injectable device such that the second signal delivery device is positioned to deliver the second electrical signal to the patient's ansa cervicalis nerve.

* * * * *

UNITED STATES PATENT AND TRADEMARK OFFICE
CERTIFICATE OF CORRECTION

| | | |
|---|---|---|
| PATENT NO. | : 12,397,160 B2 | Page 1 of 1 |
| APPLICATION NO. | : 18/637262 | |
| DATED | : August 26, 2025 | |
| INVENTOR(S) | : Richard W. O'Connor et al. | |

It is certified that error appears in the above-identified patent and that said Letters Patent is hereby corrected as shown below:

On the Title Page

On the page 4, in Column 2, under item (56) "Other Publications", Line 37, delete ""Hypogloassal" and insert -- "Hypoglossal --.

In the Specification

In Column 1, Line 9, delete "17/518,414" and insert -- 17/518,414, --.

In Column 5, Line 51, delete "glossopharangeal" and insert -- glossopharyngeal --.

In Column 6, Line 67, delete "algorithms" and insert -- algorithms. --.

In Column 19, Line 55, delete "6 mA" and insert -- 6 mA. --.

In Column 20, Line 41, delete "time;" and insert -- time. --.

In the Claims

In Column 22, Line 17, in Claim 10, delete "hypopnea" and insert -- hypopnea— --.

Signed and Sealed this
Twenty-first Day of October, 2025

John A. Squires
*Director of the United States Patent and Trademark Office*